United States Patent
Reilly et al.

(10) Patent No.: US 10,758,421 B2
(45) Date of Patent: Sep. 1, 2020

(54) DISSOLVABLE ON-COMMAND IMPLANT

(71) Applicant: CHILDREN'S NATIONAL MEDICAL CENTER, Washington, DC (US)

(72) Inventors: Brian K. Reilly, Chevy Case, MD (US); Carolyn T. Cochenour, Washington, DC (US); Peng (Patrick) Cheng, Fairfax, VA (US); Matthieu Dumont, Silver Spring, MD (US)

(73) Assignee: CHILDREN'S NATIONAL MEDICAL CENTER, Washington, DC (US)

( * ) Notice: Subject to any disclaimer, the term of this patent is extended or adjusted under 35 U.S.C. 154(b) by 1130 days.

(21) Appl. No.: 14/465,671

(22) Filed: Aug. 21, 2014

(65) Prior Publication Data
US 2015/0057590 A1    Feb. 26, 2015

Related U.S. Application Data

(60) Provisional application No. 61/868,360, filed on Aug. 21, 2013, provisional application No. 61/901,506, filed on Nov. 8, 2013.

(51) Int. Cl.
*A61F 11/00*   (2006.01)
*A61L 31/14*   (2006.01)
(Continued)

(52) U.S. Cl.
CPC .......... *A61F 11/002* (2013.01); *A61F 5/0036* (2013.01); *A61F 5/0079* (2013.01);
(Continued)

(58) Field of Classification Search
CPC ...... A61F 11/002; A61F 5/0079; A61F 6/225; A61L 31/048; A61L 31/14; A61L 31/48
See application file for complete search history.

(56) References Cited

U.S. PATENT DOCUMENTS

| | | | | |
|---|---|---|---|---|
| 3,807,409 A | * | 4/1974 | Paparella | A61F 11/002 604/264 |
| 4,650,488 A | * | 3/1987 | Bays | A61F 11/002 128/899 |

(Continued)

FOREIGN PATENT DOCUMENTS

| | | | |
|---|---|---|---|
| WO | WO 00/33774 | | 6/2000 |
| WO | WO0033774 | * | 6/2000 |

(Continued)

OTHER PUBLICATIONS

Polymers for immediate release—Evonik Health Care (https://healthcare.evonik.com/product/health-care/en/products/pharmaceutical-excipients/immediate-release/, accessed Jan. 16, 2020) (Year: 2020).*

(Continued)

*Primary Examiner* — Ariana Zimbouski
(74) *Attorney, Agent, or Firm* — Oblon, McClelland, Maier & Neustadt, L.L.P.

(57) ABSTRACT

The purpose of the "Dissolvable on-command Implant" is to act as a pressure equalizer tube in the eardrum, which has the unique characteristic that the tube can be dissolved with a specially formulated drop solution on-command. This tube can have various shapes and sizes, although the tube is usually a cylindrical tube with a hollow center, which maintains a ventilatory port for the middle ear space. With this design, the ear tube promotes drainage of middle ear fluid, lets air enter the middle ear, and allows for instillation of antibiotic drops.

14 Claims, 20 Drawing Sheets

(51) Int. Cl.
*A61L 31/04* (2006.01)
*A61F 5/00* (2006.01)
*A61F 6/22* (2006.01)
*A61F 2/04* (2013.01)

(52) U.S. Cl.
CPC ............ *A61F 6/225* (2013.01); *A61L 31/048* (2013.01); *A61L 31/14* (2013.01); *A61L 31/148* (2013.01); *A61F 2002/041* (2013.01); *A61F 2210/0004* (2013.01); *A61F 2250/003* (2013.01); *A61L 2430/14* (2013.01)

(56) References Cited

U.S. PATENT DOCUMENTS

| | | | | |
|---|---|---|---|---|
| 5,531,716 | A * | 7/1996 | Luzio | A61L 29/14 604/265 |
| 5,531,735 | A * | 7/1996 | Thompson | A61L 27/50 424/485 |
| 5,820,608 | A | 10/1998 | Luzio et al. | |
| 6,245,077 | B1 * | 6/2001 | East | A61B 17/29 606/109 |
| 6,379,323 | B1 | 4/2002 | Patterson | |
| 2004/0010306 | A1 * | 1/2004 | Freyman | A61K 9/0019 623/1.15 |
| 2005/0123520 | A1 | 6/2005 | Eavey et al. | |
| 2007/0218102 | A1 | 9/2007 | Chudzik et al. | |
| 2010/0209293 | A1 * | 8/2010 | Ikawa | A23L 3/26 422/22 |
| 2011/0229550 | A1 * | 9/2011 | Frechet | A61K 47/50 424/426 |
| 2012/0296353 | A1 * | 11/2012 | Wagner | A61F 2/064 606/153 |
| 2014/0080921 | A1 * | 3/2014 | Sheth | A61L 31/041 514/772.3 |

FOREIGN PATENT DOCUMENTS

| | | |
|---|---|---|
| WO | WO 03/059406 A2 | 7/2003 |
| WO | WO 2014/051524 A1 | 4/2014 |

OTHER PUBLICATIONS

International Search Report and Written Opinion dated Feb. 6, 2015 in PCT/US2014/052141.
Adkins AP, Friedman EM. Surgical indications and outcomes of tympanostomy tube removal. Int J Pediatr Otorhinolaryngol. Aug. 2005; 69(8):1047-51.
Bhattacharyya N. Ambulatory pediatric otolaryngologic procedures in the United States: characteristics and perioperative safety. Laryngoscope. Apr. 2010; 120(4):821-5.
Park, A. H., Hoyt, D., Britt, D., Chase, S., Tansavatdi, K., Hunter, L., McGill, L., Sheng, X., Skardal, A. and Prestwich, G. D. (2013), Cross-linked hydrogel and polyester resorbable ventilation tubes in a chinchilla model. The Laryngoscope, 123: 1043-1048. doi: 10.1002/lary.23712.
Wilder RT, Flick RP, Sprung J et. al. Early exposure to Anesthesia and Learning Disabilities in a population based birth-cohort.
Reilly, Brian Kip, and Meyers, Arlen D., Ear Tube Insertion, (2014), http://emedicine.medscace.com/article/1890757-overview.
Eudragit E Po, http://eudragit.evonik.com/product/eudragit/en/products-services/eudragit-products/protective-formulations/e-po/pades/default.aspx.

* cited by examiner

DISSOLVABLE ON-COMMAND IMPLANT

PRIORITY STATEMENT

The present invention claims benefit of priority to U.S. provisional patent application No. 61/868,360 filed on Aug. 21, 2013 and U.S. provisional patent application No. 61/901,506 filed on Nov. 8, 2013, each of which is hereby incorporated by reference in its entirety.

BACKGROUND

1. Field of the Invention

The present invention relates to medical devices, and more particularly, to a tympanostomy tube (ear tube) device used in connection with the insertion of an ear tube into a patient, and methods for softening and dissolving an ear tube on-command and without the need for anesthesia.

2. Description of the Related Art

Ear tube insertion, also known as tympanostomy or myringotomy tube insertion, is a surgical procedure for placement of a pressure equalizer tube into the tympanic membrane of the middle ear. This surgical procedure cures middle ear fluid and dramatically improves otitis media—the most common bacterial infection of early childhood. Middle ear fluid and otitis media can cause significant hearing loss and can lead to speech delays and severe ear infections. Tube insertion is particularly effective in treating otitis media because the tympanostomy tube permits the flow of antibiotic ear drops formulations into the middle ear and simultaneously allows infected ear fluid to drain out.

The first plastic tympanostomy tube was introduced in 1954. For the past 59 years there have been only minor advances in ear tube design. Current ear tubes are composed of common fluoroplastics, silicone, Teflon, or stainless steel. Ear tubes are essentially foreign bodies, which either fall out of the ear spontaneously or must be surgically removed. Normally, the tube self-extrudes from the ear as the tympanic membrane heals. If the tubes do not fall out of the eardrum after 2 to 3 years of observation, the child then undergoes a second surgery for removal.

More recently, biodegradable ear tubes have been studied by researchers. A dissolvable ear tube addresses the problems caused by the current generation of plastic tubes. Because dissolvable ear tubes do not have to be surgically removed, there is no need for further anesthesia to remove a tube that does not fall out of a child's ear on its own. Also, a biodegradable tube provides the potential benefit of lower perforation rate from a tube that stays in too long while awaiting spontaneous extrusion. However, these biodegradable tubes are designed to dissolve in the presence of body fluid, which may lead to problems. For example, biodegradable tubes begin to lose their mechanical integrity from the moment of insertion. The degradation rate is also difficult to predict because the moisture level of the middle ear varies with infection rates and amount of treatment. Further, the biodegradable tubes that have been developed dissolve too quickly to be effective and disintegrate well before the one year necessary to treat standard otitis media.

SUMMARY

Currently, there are no dissolvable on-command surgical implants for the human body. The present disclosure describes an ear tube (tympanostomy tube, ventilation tube) that will only degrade or dissolve when in contact with a specific drop formulation, such as an ear drop formulation, containing a catalyst. The "dissolvable on-command dissolvable implant" is a tube coated or constructed using a material, which will soften, degrade or dissolve only when in contact with a specific ear drop formulation. This ear tube material does not dissolve when exposed to water, soap, oil or other normal, environmental conditions.

This new dissolvable on-command ear tube is advantageous because it eliminates the need for a second surgery with anesthesia to remove the ear tubes. This approach would be a significant improvement to the current procedure and would result in substantially less trauma to the child. Furthermore, research has shown that anesthesia may have adverse side effects on a developing brain. A dissolvable on-command ear tube would provide the potential benefit of lower perforation rate and other complications from a tube that stays in too long while awaiting spontaneous extrusion.

The tube itself could be constructed in any suitable size and shape, for example a standard size and shape for ear tubes. Moreover, beyond making the ear tube with one uniform material, a different construction is also anticipated to achieve different mechanical properties and degradation profiles. The tube can be constructed such that the inner flange would dissolve more easily than the outer flanges. This is important because the outer flanges hold the tube in place such that the tube does not fall into the middle ear.

The polymer used in the fabrication of the dissolvable on-command ear tube is engineered to possess the desired mechanical properties, including rigidity, stability, and solubility in the eardrop solution. For example, the fabrication process may vary the amount of each monomer during the synthesis of the polymer. The polymer makeup of the ear tube design can be engineered to dissolve over the desired period of time, for example from a few hours to few days.

This particular polymer can be constructed into a variety of shapes and structures using techniques such as but not limited to extrusion, imprinting, spray coating, injection molding, braiding, weaving, knitting, molding, 3D printing, and machining.

In addition to using pH as a trigger for degradation, embodiments of this invention include responses to a variety of trigger mechanisms. For example, Chitosan dissolves in the presence of salt water and could be constructed to make an ear tube as well as many of the other embodiments mentioned in this document. Other potential triggers include, but are not limited to: enzymes, mechanical (i.e. ultrasound, vibration, force, etc.), electrical, temperature, chemical reaction (i.e. alcohol, acid & base, solvent, etc.), physical (i.e. light, laser, magnetic field).

The present embodiments could be used in many ear, nose, and throat procedures where a temporary implant is needed. This technology could also be applied to esophageal and gastrointestinal implant and prosthesis. Beyond stents, the present technology could be used to create implants for treating gastroesophageal reflux disease, gastro-intestinal by-pass devices for treating obesity and diabetes, and any device where it would be advantageous for the removal or disappearance of the foreign body after a period of time. Additionally, the present invention could be applied to ophthalmology, novel suture and stiches, gynecological implants and prosthesis, urological applications, etc.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

Figure 1B:
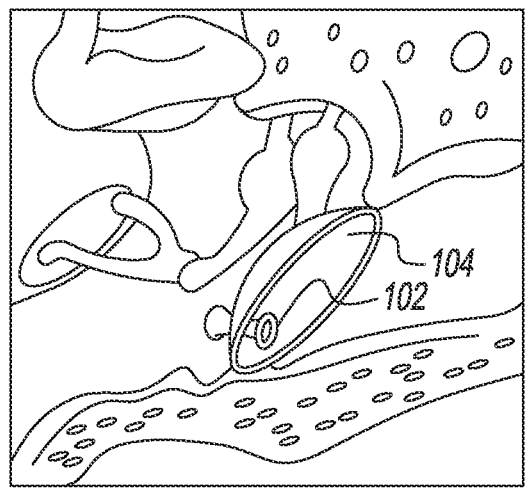
FIGS. 1A-1B illustrate the position of an exemplary embodiment of the ear tube in the eardrum according to one example.

A more complete appreciation of the present advancements and many of the attendant advantages thereof will be readily obtained as the same becomes better understood by reference to the following detailed description when considered in connection with the accompanying drawings. However, the accompanying drawings and their exemplary depictions do not in any way limit the scope of the advancements embraced by the specification. The scope of the advancements embraced by the specification and drawings are defined by the words of the accompanying claims.

Selected embodiments are now described by referring now to the drawings, wherein like reference numerals designate identical or corresponding parts throughout the several views. It is noted that, as used in the specification and the appending claims, the singular forms "a," "an," and "the" can include plural references unless the context clearly dictates otherwise.

The present embodiments disclose a bio-dissolvable ear tube and a method of creating the bio-dissolvable ear tube that maintains its mechanical integrity and clinical function until a special ear drop formulation is applied, which triggers the tube's softening, degradation or dissolution. The same on-command dissolvable property can be used in many other clinical areas.

Figure 1A:
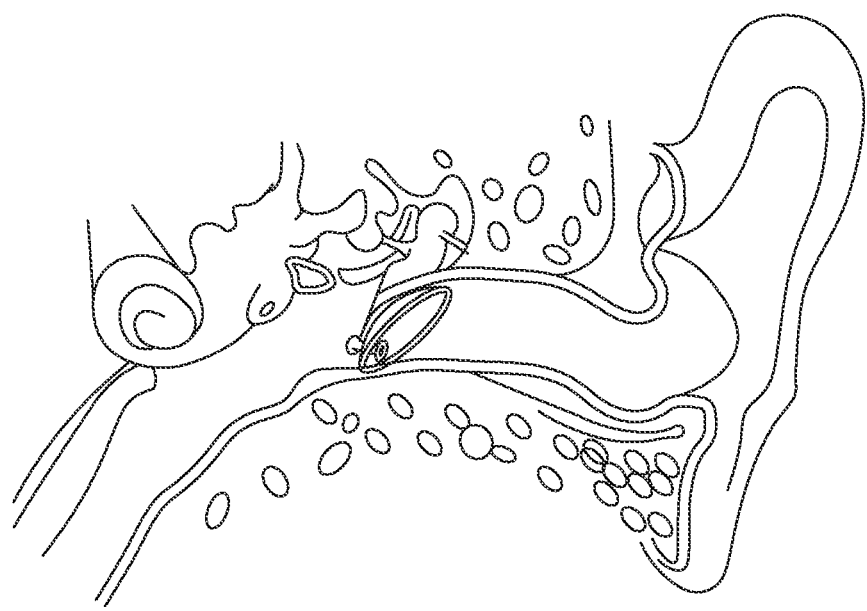
Figure 2A:
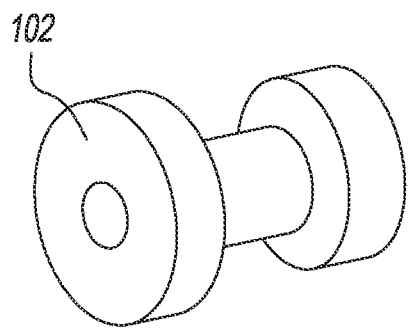
FIGS. 2A-2D illustrate an exemplary embodiment of softening, degrading and dissolution of the ear tube after the application of triggering solution drops.
Figure 2B:
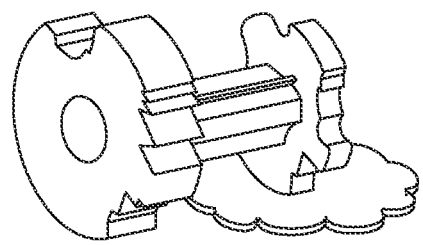
Figure 2C:
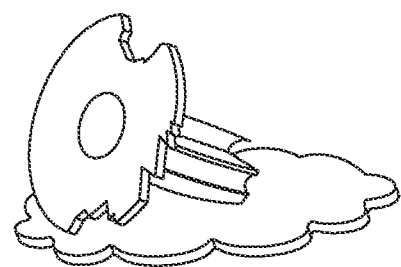
Figure 2D:
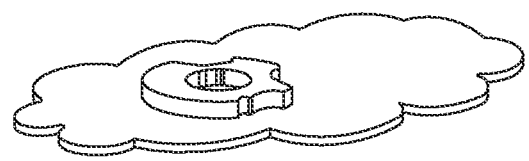

As illustrated in FIG. 1, an ear tube (tympanostomy tube, ventilation tube) 102 is implanted in an eardrum (tympanic membrane) 104. At present, there is no dissolvable on-command surgical implant for the human body. The ear tube 102 will only degrade or dissolve when in contact of a specific drop formulation, such as an ear drop formulation, containing a catalyst. The "dissolvable on-command dissolvable implant" is a tube coated or constructed using a material, which will soften, degrade or dissolve only when in contact with a specific ear drop formulation. FIGS. 2A-2D illustrate the degradation process of an ear tube composed of a polymer. FIG. 2A illustrates the ear tube in its original state, before the specific ear drop formulation, or triggering solution is applied. FIG. 2B illustrates the tube 102 degrading after the application of the triggering solution. FIG. 2C illustrates further degradation, and FIG. 2D illustrates the ear tube degrading into a liquid. The ear tube material does not dissolve when exposed to water, oil or other normal, environmental conditions.

This new dissolvable on-command ear tubes will not require the surgeon to conduct a second surgery with anesthesia to remove the ear tubes. This approach is a significant improvement to the current procedure and results in substantially less trauma to the child. The dissolvable on-command ear tube provides the potential benefit of lower perforation rate and other complications from a tube that stays in too long while awaiting spontaneous extrusion.

The dissolvable on-command ear tube could remain for the desired 6, 12, to 16 months that the clinician determines would be needed for child to outgrow the otitis media-prone time period. After resolution of the otitis media, the dissolvable on-command ear tube is easily removed with special ear drops formulation, allowing the drum to heal without any need for surgery.

The tube could be constructed in any suitable size and shape, for example a standard size and shape for ear tubes.

Figure 3A:
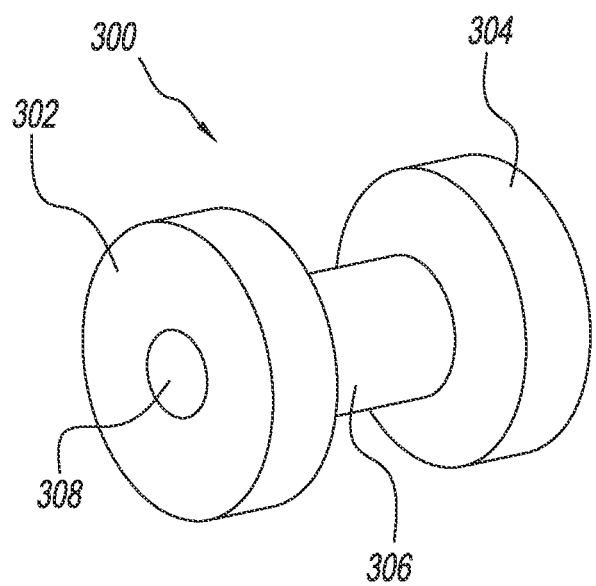
FIGS. 3A-3C illustrate a schematic isometric, side and front view of an exemplary embodiment of the ear tube according to one example.
Figure 3B:
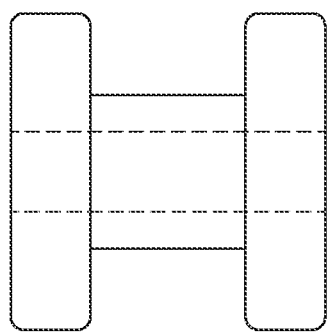
Figure 3C:
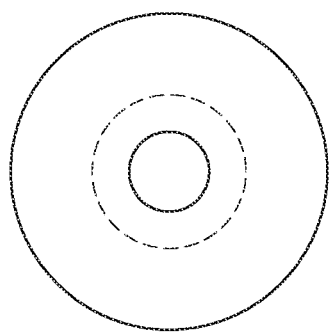
Figure 4A:
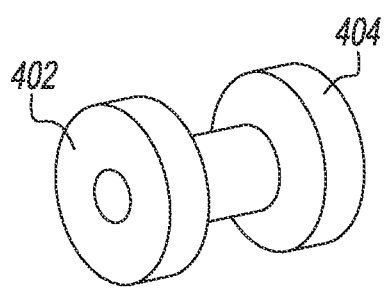
FIGS. 4A-4I illustrate alternative embodiments of the ear tube.
Figure 4B:
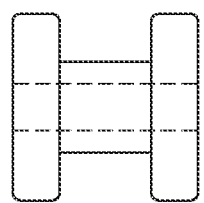
Figure 4C:
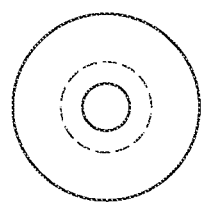
Figure 4D:
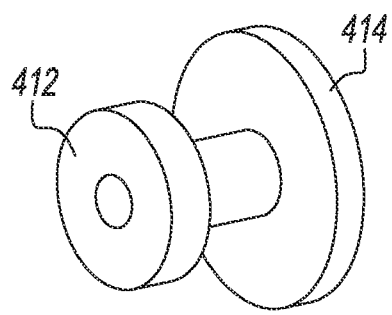
Figure 4E:
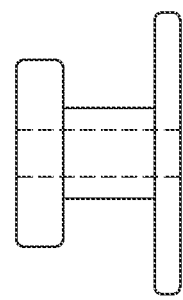
Figure 4F:
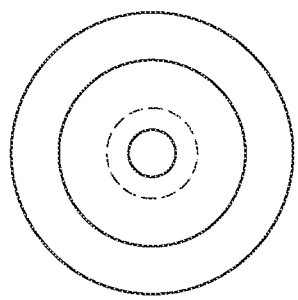
Figure 4G:
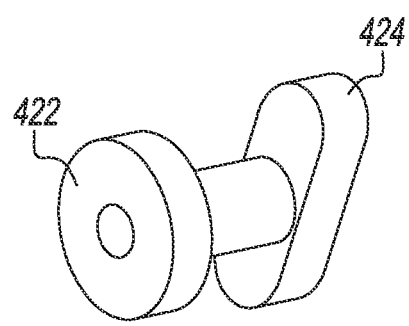
Figure 4H:
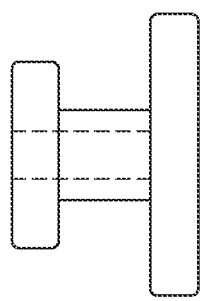
Figure 4I:
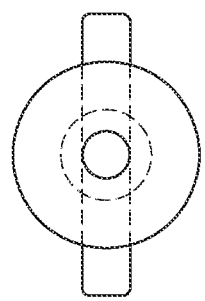

Ear tubes are constructed in a variety of shapes, mostly varying the type and size of a flange. For example, accordingly to one exemplary embodiment illustrated in FIGS. 3A-3C, the tube 300 includes an outer flange 302, an inner flange 304, a connecting member 306 and a through-hole 308. The connecting member 306 connects the outer flange 302 and the inner flange 304. The tube 300 may be a single piece of material or the tube 300 could be made of multiple materials fixed together. The through-hole extends from the outer flange 302 through the connecting member 306 to the inner flange 304. Therefore, the through-hole 308 allows the flow of antibiotic ear drops formulation into the middle ear and simultaneously allows inflected ear fluid to drain out. FIG. 3A illustrates an isometric view of the tube 300, FIG. 3B illustrates a side view, and FIG. 3C illustrates a front view.

FIG. 4 illustrates additional exemplary embodiments of the tube. For example, FIGS. 4A-4C illustrate a tube 400 wherein the outer flange 402 has the same dimensions as the inner flange 404. FIGS. 4D-F illustrates a tube 410 wherein the outer flange 412 is smaller than the inner flange 414. FIGS. 4G-I illustrate a tube 420 where the inner flange 424 is tailed, and is in the shape of a rod. The length of the tailed inner flange 424 is greater than the diameter of the inner flange 422.

In another exemplary embodiment, the design of the ear tube may be for near-permanent implantation, so that the tube would not fall out but would necessarily be removed by instillation of the dissolving ear drop formulations. However, there would still remain some possibility that the tube would naturally fall out.

Moreover, beyond making the ear tube with one uniform material, different constructions are also utilized to achieve different mechanical properties and degradation profiles. For instance, a conventional biodegradable ear tube could be coated with a polymer layer. Once the outer layer reacts to a special ear drops formulation, the internal material is exposed and the degradation process is triggered. The ear tube can also be constructed with different polymers to achieve the ideal behavior. For instance, the tube can be formed such that the inner flange would dissolve more easily than the outer flanges. This is important because the outer flanges hold the tube in place such that the tube does not fall into the middle ear.

For the dissolvable on-command ear tube, the portion inside the ear drum must dissolve/disintegrate first, so that the remaining structure will fall out of the ear, instead of falling into the middle ear.

Figure 5:
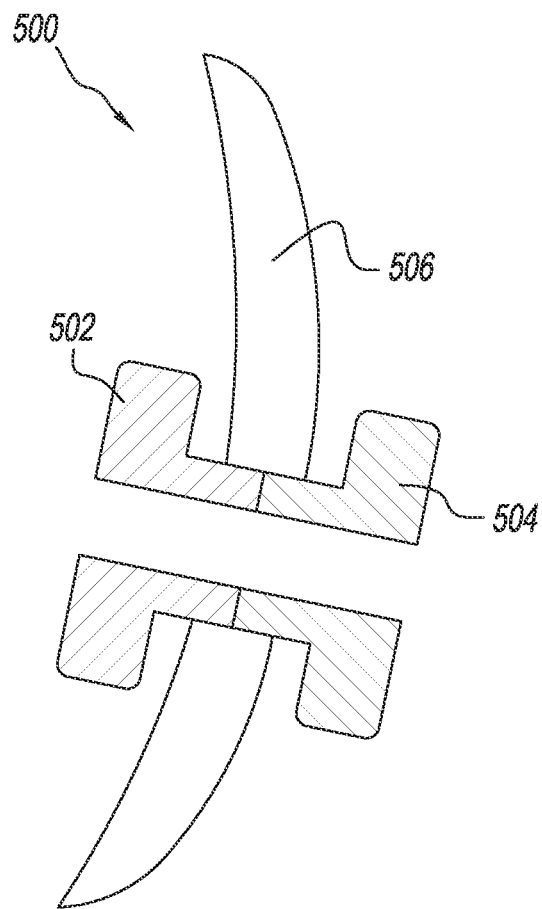
FIG. 5 illustrates a cross-sectional view of an exemplary embodiment of an ear tube placed in the eardrum with a two-material construction.

FIG. 5 illustrates an exemplary embodiment in a cross-sectional view. A tube 500 is constructed of two different polymers. The outer portion 502 may be constructed of a polymer that is degradable on-command. The inner portion 504 of the tube may be constructed of a bio-absorbable polymer. The outer portion 502 is the portion of the tube 500 that is outside the eardrum, and the inner portion 504 is the portion that is inside the ear drum 506.

Figure 6:
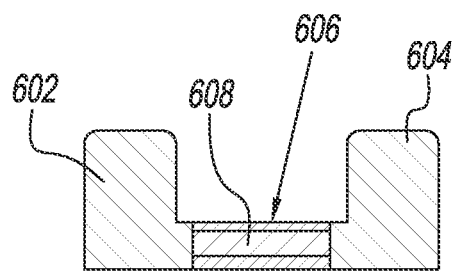
FIG. 6 illustrates a cross-sectional view of an exemplary embodiment multi-component ear tube.
Figure 6:
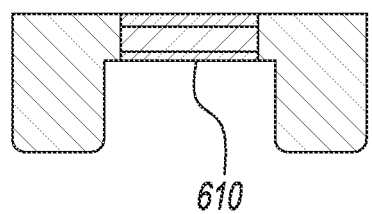

FIG. 6 illustrates another exemplary embodiment, wherein the tube 600 is constructed from multiple components. The outer flange 602 and the inner flange 604 may be constructed from a slowly degrading polymer. The connecting member 606 may be constructed of a fast degrading polymer 608. The connecting member may also have a coating 610 applied, in which the coating 610 is reactive to alcohols, oils, acid, alkali, temperature, light, or the like. Thereby, the connecting member 606 will degrade on-command, at faster rate than the outer flange 602 and the inner flange 604.

Figure 7A:
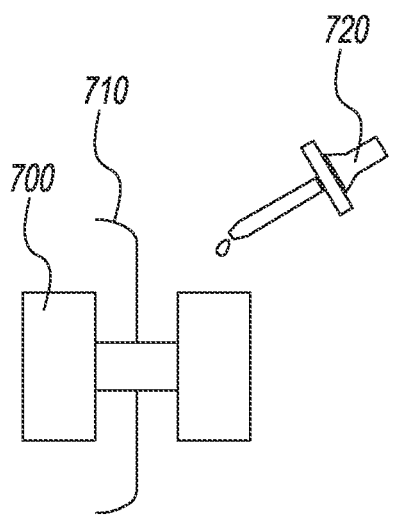
FIGS. 7A-7E illustrate an exemplary embodiment of the dissolution mechanism for the ear tube following the addition of eardrops.
Figure 7B:
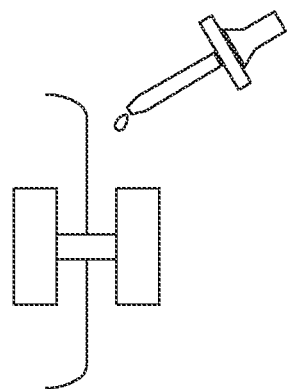
Figure 7C:
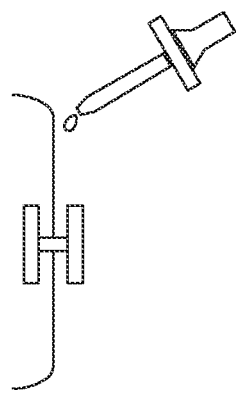
Figure 7D:
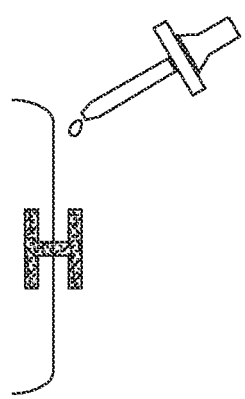
Figure 7E:

FIGS. 7A-7E illustrate another exemplary embodiment wherein the tube 700 gradually dissolves over the course of several doses of the triggering solution. FIG. 7A illustrates the tube 700 implanted in the ear drum 710. A triggering solution 720 is applied to the tube 700, which causes the ear tube to gradually dissolve. FIG. 7B illustrates a second dose of the trigger solution, 7C a third dose, and 7D a fourth dose. FIG. 7E illustrates that the tube 700 has completely dissolved. The number of doses may fluctuate depending on the material of the tube 700, the triggering solution 720, and the desire of the clinician.

Figure 8:
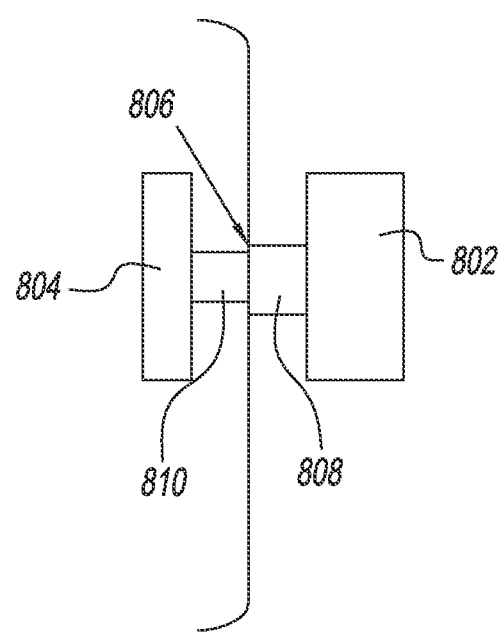
FIG. 8 illustrates an exemplary embodiment of an ear tube where the inner portion of the tube inside the middle ear is thinner.

FIG. 8 illustrates another exemplary embodiment wherein the thickness of connecting member 806 of the ear tube 800 can vary along the length of the connecting member 806 so that the thinner sections dissolve first. For example, the outer flange 802 and the inner flange 804 may be the same dimensions or alternatively may be different sizes or shapes. The outer portion 808 of the connecting member 806 has a larger diameter than the inner portion 810 of the connecting member 806. Alternatively, the diameter of the connecting member 806 may vary from a larger diameter at one end, to a smaller diameter at the other end.

Figure 9A:
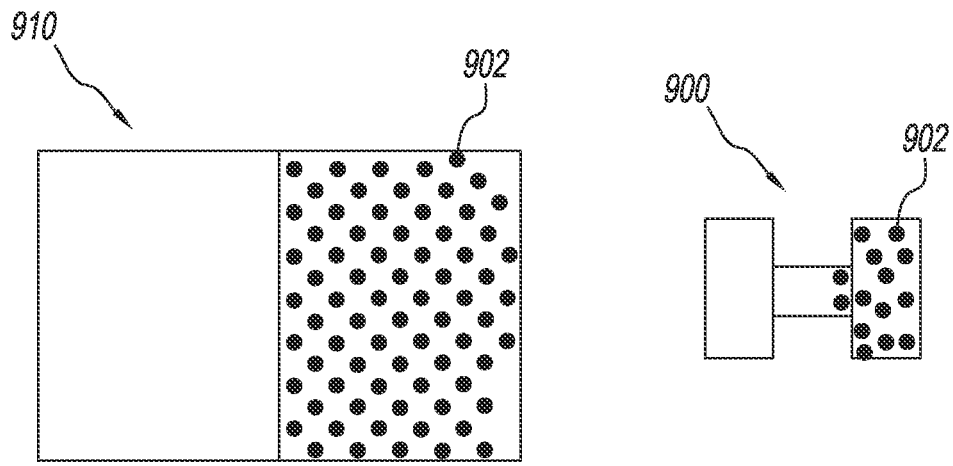
FIG. 9A illustrates an exemplary embodiment of a polymer block and ear tube with half of the ear tube mixed with micro particles.
Figure 9B:
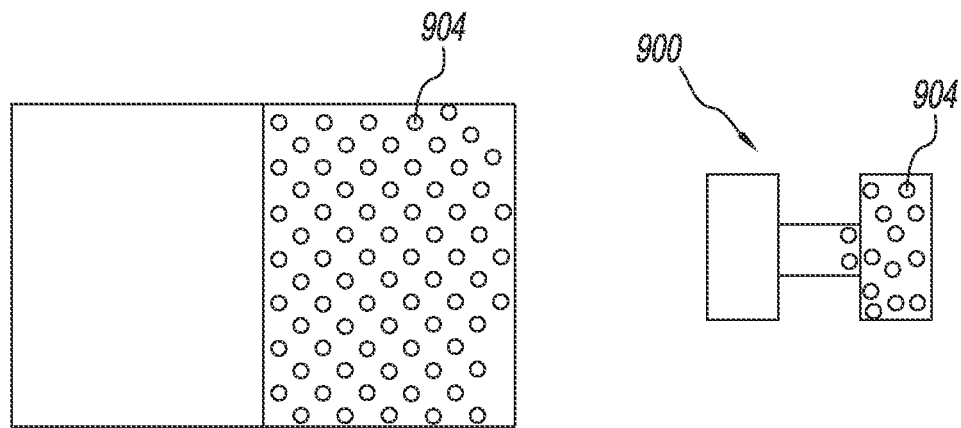
FIG. 9B illustrates an exemplary embodiment of a polymer block and ear tube after the micro particles have dissolved.

Turning a polymer from powder form into solid block drastically reduces the surface area of the polymer, making the polymer dissolve much slower in solid form than in powder form. This characteristic is a desirable feature and provides benefits in the present context. A target polymer will dissolve/disintegrate within a reasonably short period of time once the triggering solution is applied. According in an exemplary embodiment, the surface area of the polymer could be increased by adding salt, sugar or other particles into the polymer mixture. The particles may be later dissolved away by using water or another solution, keeping the polymer structure in place while creating micro-cavities inside the polymer. This process is illustrated in FIGS. 9A-9B. FIG. 9A illustrates a polymer of the tube 900 and a polymer block 910 that includes particles 902 in the mixture when the tube 900 is formed. The particles 902 are then dissolved, and micro-cavities 904 are created in the tube 900 and in the polymer block 910, as illustrated in FIG. 9B. A tube 900 could then be manufactured from the polymer block 910.

Alternatively, in another exemplary embodiment, the dissolving solution can be applied multiple times over a period of several days so that each administration of the solution removes a layer until the entire tube is gone.

In another exemplary embodiment, the inner portion of the ear tube could be fabricated out of a porous structure and could be used to achieve the same purpose. As shown in FIG. 9, a two part structure with parts that have micro-cavities can be created to allow portions of the structure to dissolve faster than the rest of the tube without micro-cavities. These micro-cavities could be created by mixing salt or sugar particles with the polymer, and later dissolved away in water or another solution that will not affect the polymer structure. Thus the micro-cavities allow additional surface area for the triggering solution to come in contact with thereby increasing the rate of disintegration.

Figure 10:
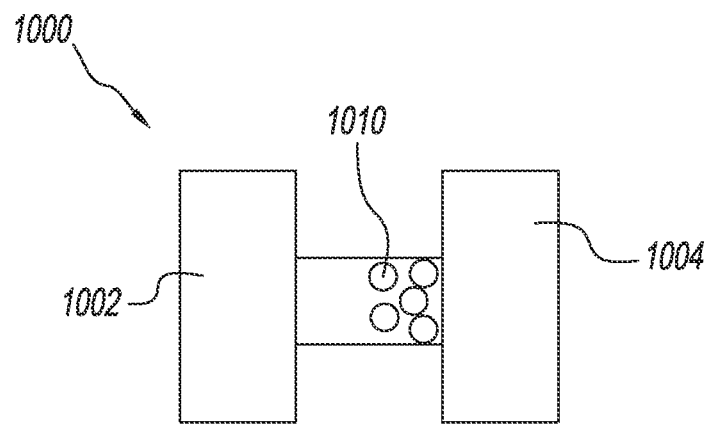
FIG. 10 illustrates an exemplary embodiment of the ear tube with an E-PO polymer and biodegradable polymer.
Figure 11:
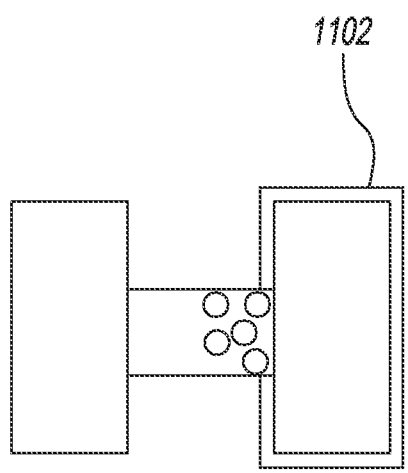
FIG. 11 illustrates an exemplary embodiment of the ear tube with E-PO polymer and biodegradable polymer covered by an E-PO coating.
Figure 12A:
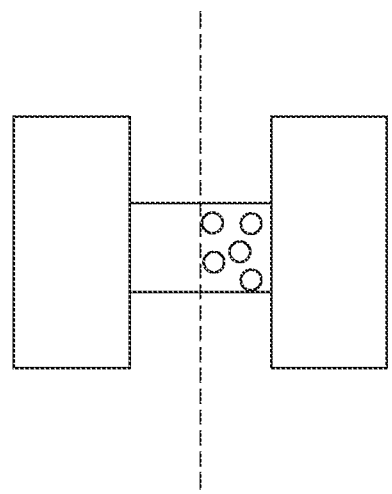
FIGS. 12A-12B illustrates a schematic representing an exemplary embodiment for the ear tube with the center part made out of porous E-PO polymer.
Figure 12B:
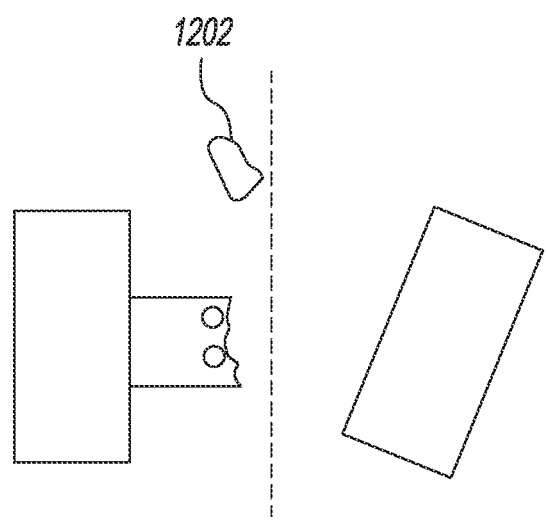

As illustrated in FIGS. 10 and 11, the inner flange 1004 of the ear tube inside the ear drum could be made of bio-absorbable materials. Further, a portion of the connecting member 1006 near the inner flange 1004 may have micro-cavities 1010. When a triggering solution 1202, such as ethanol, is applied, the connecting member of the ear tube with micro-cavities will absorb the solution and disintegrate first, thus breaking the ear tube into two parts, as illustrated in FIGS. 12A-12B. The inner flange that remains in the middle ear made of biodegradable material will eventually be absorbed. Alternatively, an E-PO polymer coating 1102, illustrated in FIG. 11, could be applied to the inner flange 1004. The E-PO polymer coating may protect the biodegradable polymer from degradation before the triggering solution is applied. When the triggering solution is applied, the E-PO polymer degrades and exposes the biodegradable polymer which will naturally degrade over time.

The shape and structure of the ear tube could be specially fabricated from a polymer so when the ear drops formulations are applied, the triggered reaction dissolves the ear tube in a specific way. In this way, the ear tube dissolves more evenly. The polymer of the ear tube can be engineered to possess the desired mechanical properties, including rigidity, stability, and solubility in the acidic solution. For example, the fabrication process may vary the amount of each monomer during the synthesis of the polymer. The polymer makeup of the ear tube design can be engineered to dissolve over the desired period of time, for example, from a few hours to few days.

Materials used for dissolvable on-command implant may include but are not limited to: Dextran, chitosan, carbohydrates, gelatin, collagen, polyvinyl pyrrolidone (PVP), polyvinyl alcohol, polyethylene glycol diacrylate, acrylate polymers and combinations of the above. Dextran is a complex, branched polysaccharide composed of chains of varying lengths from about 3 to about 2000 kDa. Chitosan is a linear polysaccharide composed of randomly distributed β-(1-4)-linked D-glucosamine (deacetylated unit) and N-acetyl-D-glucosamine (acetylated unit). The carbohydrates include monosaccharides, disaccharides, oligosaccharides, and polysaccharides. The gelatin is a substance derived from hydrolyzed collagen. The polyvinyl pyrrolidone (PVP) is a polymer made from repeating monomer N-vinylpyrrolidone units. Other names for PVP are polyvidone and povidone. The polyvinyl alcohol includes PVOH, PVA, and PVAl. The polyethylene glycol diacrylate is polyethylene glycol terminated with acrylate groups.

Polymers for dissolvable on-command implant may include but are not limited to: acrylic polymers and copolymers architecture, chain length and monomer arrangements. The polymers architecture may include: block copolymer, star polymer, comb polymer, brush polymer, $AB_2$ star, palm-tree $AB_n$, H-shaped $B_2AB_2$, Dumbell, Pom-pom, ring block, star block $AB_n$ coil-cycle-coil, star $A_nB_n$. The monomer arrangement may include: Alternating copolymers, periodic copolymers, statistical copolymers, random copolymers, Bock copolymers, graft or grafted copolymers. The monomer may include: Acrylamide and Methacrylamide, Acrylates, Acrylic Acids and Salts, Acrylonitriles, Bisphenol Acrylics, Fluorinated Acrylics, Maleimides, Methacrylates, and Polyfunctional Acrylics as listed in Table 1 to Table 9.

TABLE 1

List of Acrylamides and Methacrylamides monomers.

| Acrylamide and Methacrylamide | formula |
|---|---|
| 2-Acrylamido-2-methyl-1-propanesulfonic acid | $C_7H_{13}NO_4S$ |
| 2-Acrylamido-2-methyl-1-propanesulfonic acid | $C_7H_{12}NNaO_4S$ |
| 3-(Acrylamido)phenylboronic acid | $C_9H_{10}BNO_3$ |
| (3-Acrylamidopropyl)trimethylammonium chloride | $C_9H_{19}ClN_2O$ |
| N-Acryloylamido-ethoxyethanol | $C_7H_{13}NO_3$ |
| Alkylacrylamide | |
| N-(3-Aminopropyl)methacrylamide hydrochloride | $C_7H_{14}N_2O \cdot HCl$ |
| N-tert-Butylacrylamide | $C_7H_{13}NO$ |
| Diacetone acrylamide | $C_9H_{15}NO_2$ |
| N,N-Diethylacrylamide | $C_7H_{13}NO$ |

TABLE 1-continued

List of Acrylamides and Methacrylamides monomers.

| Acrylamide and Methacrylamide | formula |
|---|---|
| N,N-Diethylmethacrylamide | $C_8H_{15}NO$ |
| N,N-Dimethylacrylamide | $C_5H_9NO$ |
| N-[3-(Dimethylamino)propyl]methacrylamide | $C_9H_{18}N_2O$ |
| N-Diphenylmethylacrylamide | $C_{16}H_{15}NO$ |
| N-Ethylacrylamide | $C_5H_9NO$ |
| N,N'-Hexamethylenebis(methacrylamide) | $C_{14}H_{24}N_2O_2$ |
| N-Hydroxyethyl acrylamide | $C_5H_9NO_2$ |
| N-(Hydroxymethyl)acrylamide | $C_4H_7NO_2$ |
| N-(Isobutoxymethyl)acrylamide | $C_8H_{15}NO_2$ |
| N-Isopropylacrylamide | $C_6H_{11}NO$ |
| N-Isopropylacrylamide | $C_6H_{11}NO$ |
| N-Isopropylmethacrylamide | $C_7H_{13}NO$ |
| Methacrylamide | $C_4H_7NO$ |
| N-(3-Methoxypropyl)acrylamide | $C_7H_{13}NO_2$ |
| N-Phenylacrylamide | $C_9H_9NO$ |
| N-(Triphenylmethyl)methacrylamide | $C_{23}H_{21}NO$ |
| N-[Tris(hydroxymethyl)methyl]acrylamide | $C_7H_{13}NO_4$ |

TABLE 2

List of Acrylates monomers.

| Acrylates | formula |
|---|---|
| 4-Acetoxyphenethyl acrylate | $C_{13}H_{14}O_4$ |
| Acryloyl chloride | $C_3H_3ClO$ |
| Acryloyl chloride | $C_3H_3ClO$ |
| 4-Acryloylmorpholine | $C_7H_{11}NO_2$ |
| [2-(Acryloyloxy)ethyl]trimethylammonium chloride | $C_8H_{16}ClNO_2$ |
| 2-(4-Benzoyl-3-hydroxyphenoxy)ethyl acrylate | $C_{18}H_{16}O_5$ |
| Benzyl 2-propylacrylate | $C_{13}H_{16}O_2$ |
| Butyl acrylate | $C_7H_{12}O_2$ |
| tert-Butyl acrylate | $C_7H_{12}O_2$ |
| 2-[[(Butylamino)carbonyl]oxy]ethyl acrylate | $C_{10}H_{17}NO_4$ |
| tert-Butyl 2-bromoacrylate | $C_7H_{11}BrO_2$ |
| 4-tert-Butylcyclohexyl acrylate | $C_{13}H_{22}O_2$ |
| 2-Carboxyethyl acrylate | $C_6H_8O_4$ |
| 2-Carboxyethyl acrylate oligomers | |
| 2-Chloroethyl acrylate contains >100 ppm MEHQ as inhibitor, 97% | $C_5H_7ClO_2$ |
| 2-(Diethylamino)ethyl acrylate | $C_9H_{17}NO_2$ |
| Di(ethylene glycol) ethyl ether acrylate | $C_9H_{16}O_4$ |
| Di(ethylene glycol) 2-ethylhexyl ether acrylate | $C_{15}H_{28}O_4$ |
| 2-(Dimethylamino)ethyl acrylate | $C_7H_{13}NO_2$ |
| 3-(Dimethylamino)propyl acrylate | $C_8H_{15}NO_2$ |
| Dipentaerythritol penta-/hexa-acrylate | $C_{25}H_{32}O_{12}$ |
| Ethyl acrylate | $C_5H_8O_2$ |
| 2-Ethylacryloyl chloride | $C_5H_7ClO$ |
| Ethyl 2-(bromomethyl)acrylate | $C_6H_9BrO_2$ |
| Ethyl cis-(β-cyano)acrylate | $C_6H_7NO_2$ |
| Ethylene glycol dicyclopentenyl ether acrylate | $C_{15}H_{20}O_3$ |
| Ethylene glycol methyl ether acrylate | $C_6H_{10}O_3$ |
| Ethylene glycol phenyl ether acrylate | $C_{11}H_{12}O_3$ |
| Ethyl 2-ethylacrylate | $C_7H_{12}O_2$ |
| 2-Ethylhexyl acrylate | $C_{11}H_{20}O_2$ |
| Ethyl 2-propylacrylate | $C_8H_{14}O_2$ |
| Ethyl 2-(trimethylsilylmethyl)acrylate | $C_9H_{18}O_2Si$ |
| Hexyl acrylate | $C_9H_{16}O_2$ |
| 4-Hydroxybutyl acrylate | $C_7H_{12}O_3$ |
| 2-Hydroxyethyl acrylate | $C_5H_8O_3$ |
| 2-Hydroxy-3-phenoxypropyl acrylate | $C_{12}H_{14}O_4$ |
| Hydroxypropyl acrylate | $C_6H_{10}O_3$ |
| Isobornyl acrylate | $C_{13}H_{20}O_2$ |
| Isobutyl acrylate | $C_7H_{12}O_2$ |
| Isodecyl acrylate | $C_{13}H_{24}O_2$ |
| Isooctyl acrylate | $C_{11}H_{20}O_2$ |
| Lauryl acrylate | $C_{15}H_{28}O_2$ |
| Methyl 2-acetamidoacrylate | $C_6H_9NO_3$ |
| Methyl acrylate | $C_4H_6O_2$ |
| Methyl α-bromoacrylate | $C_4H_5BrO_2$ |
| Methyl 2-(bromomethyl)acrylate | $C_5H_7BrO_2$ |
| Methyl 2-(chloromethyl)acrylate | $C_5H_7ClO_2$ |
| Methyl 3-hydroxy-2-methylenebutyrate | $C_6H_{10}O_3$ |

TABLE 2-continued

List of Acrylates monomers.

| Acrylates | formula |
|---|---|
| Methyl 2-(trifluoromethyl)acrylate | $C_5H_5F_3O_2$ |
| Octadecyl acrylate | $C_{21}H_{40}O_2$ |
| Pentabromobenzyl acrylate | $C_{10}H_5Br_5O_2$ |
| Pentabromophenyl acrylate | $C_9H_3Br_5O_2$ |
| Pentafluorophenyl acrylate | $C_9H_3F_5O_2$ |
| Poly(ethylene glycol) diacrylate | |
| Poly(ethylene glycol) methyl ether acrylate | |
| Poly(propylene glycol) acrylate | |
| Soybean oil, epoxidized acrylate | |
| 3-Sulfopropyl acrylate | $C_6H_9KO_5S$ |
| Tetrahydrofurfuryl acrylate | $C_8H_{12}O_3$ |
| 3-(Trimethoxysilyl)propyl acrylate | $C_9H_{18}O_5Si$ |
| 3,5,5-Trimethylhexyl acrylate | |
| 10-Undecenyl acrylate | $C_{14}H_{24}O_2$ |

TABLE 3

List of Acrylic Acids and Salts monomers.

| Acrylic Acids and Salts | formula |
|---|---|
| Acrylic acid anhydrous | $C_3H_4O_2$ |
| 2-Bromoacrylic acid | $C_3H_3BrO_2$ |
| 2-(Bromomethyl)acrylic acid | $C_4H_5BrO_2$ |
| 2-Ethylacrylic acid | $C_5H_8O_2$ |
| Hafnium carboxyethyl acrylate | $C_{24}H_{28}HfO_{16}$ |
| Methacrylic acid | $C_4H_6O_2$ |
| 2-Propylacrylic acid | $C_6H_{10}O_2$ |
| Sodium acrylate | $C_3H_3NaO_2$ |
| Sodium methacrylate | $C_4H_5NaO_2$ |
| 2-(Trifluoromethyl)acrylic acid | $C_4H_3F_3O_2$ |
| Zinc acrylate | $C_6H_6O_4Zn$ |
| Zirconium acrylate | $C_{12}H_{12}O_8Zr$ |
| Zirconium bromonorbornanelactone carboxylate triacrylate | |
| Zirconium carboxyethyl acrylate | $C_{24}H_{28}O_{16}Zr$ |

TABLE 4

List of Acrylonitriles monomers.

| Acrylonitriles | formula |
|---|---|
| Acrylonitrile | $C_3H_3N$ |
| 1-Cyanovinyl acetate | $C_5H_5NO_2$ |
| Ethyl 2-cyanoacrylate | $C_6H_7NO_2$ |

TABLE 5

List of Bisphenol Acrylic monomers.

| Bisphenol Acrylics | formula |
|---|---|
| Bisphenol A ethoxylate diacrylate average $M_n$ ~468 | |
| Bisphenol A ethoxylate diacrylate average $M_n$ ~512 | |
| Bisphenol A ethoxylate diacrylate average $M_n$ ~688 | |
| Bisphenol A ethoxylate dimethacrylate average $M_n$ ~1,700 | |
| Bisphenol A glycerolate dimethacrylate glycerol/phenol 1 | $C_{29}H_{36}O_8$ |
| Bisphenol A glycerolate (1 glycerol/phenol) diacrylate | $C_{27}H_{32}O_8$ |
| Bisphenol A dimethacrylate | $C_{23}H_{24}O_4$ |
| Bisphenol F ethoxylate (2 EO/phenol) diacrylate average $M_n$ ~484 | |

TABLE 6

List of Fluorinated Acrylics monomers.

| Fluorinated Acrylics | formula |
|---|---|
| 2,2,3,3,4,4,5,5,6,6,7,7-Dodecafluoroheptyl acrylate | $C_{10}H_6F_{12}O_2$ |
| 3,3,4,4,5,5,6,6,7,7,8,8,9,9,10,10,11,11,12,12,12-Heneicosafluorododecyl acrylate | $C_{15}H_7F_{21}O_2$ |
| 3,3,4,4,5,5,6,6,7,7,8,8,9,9,10,10,11,11,12,12,12-Heneicosafluorododecyl methacrylate | $C_{16}H_9F_{21}O_2$ |
| 3,3,4,4,5,5,6,6,7,7,8,8,9,9,10,10,10-Heptadecafluorodecyl methacrylate | $C_{14}H_9F_{17}O_2$ |
| 2,2,3,3,4,4,4-Heptafluorobutyl acrylate | $C_7H_5F_7O_2$ |
| 2,2,3,3,4,4,4-Heptafluorobutyl methacrylate | $C_8H_7F_7O_2$ |
| 2,2,3,4,4,4-Hexafluorobutyl acrylate | $C_7H_6F_6O_2$ |
| 2,2,3,4,4,4-Hexafluorobutyl methacrylate | $C_8H_8F_6O_2$ |
| 1,1,1,3,3,3-Hexafluoroisopropyl acrylate | $C_6H_4F_6O_2$ |
| 1,1,1,3,3,3-Hexafluoroisopropyl methacrylate | $C_7H_6F_6O_2$ |
| 2,2,3,3,4,4,5,5-Octafluoropentyl acrylate | $C_8H_6F_8O_2$ |
| 2,2,3,3,4,4,5,5-Octafluoropentyl methacrylate | $C_9H_8F_8O_2$ |
| 2,2,3,3,3-Pentafluoropropyl acrylate | $C_6H_5F_5O_2$ |
| 2,2,3,3,3-Pentafluoropropyl methacrylate | $C_7H_7F_5O_2$ |
| 1H,1H,2H,2H-Perfluorodecyl acrylate | $C_{13}H_7F_{17}O_2$ |
| 2,2,3,3-Tetrafluoropropyl methacrylate | $C_7H_8F_4O_2$ |
| 3,3,4,4,5,5,6,6,7,7,8,8,8-Tridecafluorooctyl acrylate | $C_{11}H_7F_{13}O_2$ |
| 3,3,4,4,5,5,6,6,7,7,8,8,8-Tridecafluorooctyl methacrylate | $C_{12}H_9F_{13}O_2$ |
| 2,2,2-Trifluoroethyl methacrylate | $C_6H_7F_3O_2$ |
| 1,1,1-Trifluoro-2-(trifluoromethyl)-2-hydroxy-4-methyl-5-pentylmethacrylate | $C_{11}H_{14}F_6O_3$ |
| 2-[(1',1',1'-Trifluoro-2'-(trifluoromethyl)-2'-hydroxy)propyl]-3-norbornyl methacrylate | $C_{15}H_{18}F_6O_3$ |

TABLE 7

List of Maleimides monomers.

| Maleimides | formula |
|---|---|
| 2-[8-(3-Hexyl-2,6-dioctylcyclohexyl)octyl]pyromellitic diimide | |
| N,N'-(o-Phenylene)dimaleimide 99% | $C_{14}H_8N_2O_4$ |
| N,N'-(1,4-Phenylene)dimaleimide 97% | $C_{14}H_8N_2O_4$ |

TABLE 8

List of Methacrylates monomers.

| Methacrylates | formula |
|---|---|
| Allyl methacrylate | $C_7H_{10}O_2$ |
| 2-Aminoethyl methacrylate hydrochloride | $C_6H_{11}NO_2 \cdot HCl$ |
| 2-[3-(2H-Benzotriazol-2-yl)-4-hydroxyphenyl]ethyl methacrylate | $C_{18}H_{17}N_3O_3$ |
| Benzyl methacrylate | $C_{11}H_{12}O_2$ |
| Bis(2-methacryloyl)oxyethyl disulfide | $C_{12}H_{18}O_4S_2$ |
| 2-(2-Bromoisobutyryloxy)ethyl methacrylate | $C_{10}H_{15}BrO_4$ |
| 2-(tert-Butylamino)ethyl methacrylate | $C_{10}H_{19}NO_2$ |
| Butyl methacrylate | $C_8H_{14}O_2$ |
| tert-Butyl methacrylate | $C_8H_{14}O_2$ |
| 9H-Carbazole-9-ethylmethacrylate | $C_{18}H_{17}NO_2$ |
| 3-Chloro-2-hydroxypropyl methacrylate | $C_7H_{11}ClO_3$ |
| Cyclohexyl methacrylate | $C_{10}H_{16}O_2$ |
| 2-(Diethylamino)ethyl methacrylate | $C_{10}H_{19}NO_2$ |
| Diethylene glycol butyl ether methacrylate | $C_{12}H_{22}O_4$ |
| Di(ethylene glycol) methyl ether methacrylate | $C_9H_{16}O_4$ |
| 2-(Diisopropylamino)ethyl methacrylate | $C_{12}H_{23}NO_2$ |
| 2-(Dimethylamino)ethyl methacrylate | $C_8H_{15}NO_2$ |
| 2-Ethoxyethyl methacrylate | $C_8H_{14}O_3$ |
| Ethylene glycol dicyclopentenyl ether methacrylate | $C_{16}H_{22}O_3$ |
| Ethylene glycol methyl ether methacrylate | $C_7H_{12}O_3$ |
| Ethylene glycol phenyl ether methacrylate | $C_{12}H_{14}O_3$ |
| 2-Ethylhexyl methacrylate | $C_{12}H_{22}O_2$ |
| Ethyl methacrylate | $C_6H_{10}O_2$ |
| Ferrocenylmethyl methacrylate | $C_{15}H_{16}FeO_2$ |
| Furfuryl methacrylate | $C_9H_{10}O_3$ |
| Glycidyl methacrylate | $C_7H_{10}O_3$ |

TABLE 8-continued

List of Methacrylates monomers.

| Methacrylates | formula |
|---|---|
| Glycosyloxyethyl methacrylate | $C_{12}H_{20}O_8$ |
| Hexyl methacrylate | $C_{10}H_{18}O_2$ |
| Hydroxybutyl methacrylate | $C_8H_{14}O_3$ |
| 2-Hydroxyethyl methacrylate | $C_6H_{10}O_3$ |
| 2-Hydroxyethyl methacrylate | $C_6H_{10}O_3$ |
| Hydroxypropyl methacrylate | |
| 2-Hydroxypropyl 2-(methacryloyloxy)ethyl phthalate | $C_{17}H_{20}O_7$ |
| 2-Hydroxy-3-{3-[2,4,6,8-tetramethyl-4,6,8-tris(propyl glycidyl ether)-2-cyclotetrasiloxanyl]propoxy}propyl methacrylate | $C_{32}H_{62}O_{14}Si_4$ |
| Isobornyl methacrylate | $C_{14}H_{22}O_2$ |
| Isobutyl methacrylate | $C_8H_{14}O_2$ |
| 2-Isocyanatoethyl methacrylate | $C_7H_9NO_3$ |
| Isodecyl methacrylate | $C_{14}H_{26}O_2$ |
| Lauryl methacrylate | $C_{16}H_{30}O_2$ |
| Methacrylic acid N-hydroxysuccinimide ester | $C_8H_9NO_4$ |
| [3-(Methacryloylamino)propyl]dimethyl(3-sulfopropyl)ammonium hydroxide | $C_{12}H_{24}N_2O_4S$ |
| [3-(Methacryloylamino)propyl]trimethylammonium chloride | $C_{10}H_{21}ClN_2O$ |
| Methacryloyl chloride | $C_4H_5ClO$ |
| Methacryloyl chloride | $C_4H_5ClO$ |
| [2-(Methacryloyloxy)ethyl]dimethyl-(3-sulfopropyl)ammonium hydroxide | $C_{11}H_{21}NO_5S$ |
| 2-Methacryloyloxyethyl phosphorylcholine | $C_{11}H_{22}NO_6P$ |
| [2-(Methacryloyloxy)ethyl]trimethylammonium chloride | $C_9H_{18}ClNO_2$ |
| Methyl methacrylate | $C_5H_8O_2$ |
| 2-(Methylthio)ethyl methacrylate | $C_7H_{12}O_2S$ |
| mono-2-(Methacryloyloxy)ethyl maleate | $C_{10}H_{12}O_6$ |
| mono-2-(Methacryloyloxy)ethyl succinate | $C_{10}H_{14}O_6$ |
| 2-N-Morpholinoethyl methacrylate | $C_{10}H_{17}NO_3$ |
| 1-Naphthyl methacrylate | $C_{14}H_{12}O_2$ |
| 2-(2-Oxo-1-imidazolidinyl)ethyl methacrylate | $C_9H_{14}N_2O_3$ |
| Pentabromophenyl methacrylate | $C_{10}H_5Br_5O_2$ |
| Pentafluorophenyl methacrylate | $C_{10}H_5F_5O_2$ |
| 1,4-Phenylene dimethacrylate | $C_{14}H_{14}O_4$ |
| Phenyl methacrylate | $C_{10}H_{10}O_2$ |
| Phosphoric acid 2-hydroxyethyl methacrylate ester | |
| Poly(ethylene glycol) behenyl ether methacrylate | |
| Poly(ethylene glycol) 2,4,6-tris(1-phenylethyl)phenyl ether methacrylate | |
| Poly(propylene glycol) methacrylate | |
| Propyl methacrylate | $C_7H_{12}O_2$ |
| 1-Pyrenemethyl methacrylate | $C_{21}H_{16}O_2$ |
| Solketal methacrylate | $C_{10}H_{16}O_4$ |
| Stearyl methacrylate | $C_{22}H_{42}O_2$ |
| 3-Sulfopropyl methacrylate | $C_7H_{11}KO_5S$ |
| TEMPO methacrylate | $C_{13}H_{22}NO_3$ |
| Tetrahydrofurfuryl methacrylate | $C_9H_{14}O_3$ |
| 3-(Trichlorosilyl)propyl methacrylate | $C_7H_{11}Cl_3O_2Si$ |
| Triethylene glycol methyl ether methacrylate | $C_{11}H_{20}O_5$ |
| 1,1,1-Trifluoro-2-(trifluoromethyl)-2-hydroxy-4-methyl-5-pentyl methacrylate | $C_{11}H_{14}F_6O_3$ |
| 2-[(1',1',1'-Trifluoro-2'-(trifluoromethyl)-2'-hydroxy)propyl]-3-norbornyl methacrylate | $C_{15}H_{18}F_6O_3$ |
| 3-(Trimethoxysilyl)propyl methacrylate | $C_{10}H_{20}O_5Si$ |
| 3,3,5-Trimethylcyclohexyl methacrylate | $C_{13}H_{22}O_2$ |
| (Trimethylsilyl)methacrylate | $C_7H_{14}O_2Si$ |
| 2-(Trimethylsilyloxy)ethyl methacrylate | $C_9H_{18}O_3Si$ |
| 3-[Tris(trimethylsiloxy)silyl]propyl methacrylate | $C_{16}H_{38}O_5Si_4$ |
| Vinyl methacrylate | $C_6H_8O_2$ |

TABLE 9

List of Polyfunctional Acrylics monomers.

| Polyfunctional Acrylics | formula |
|---|---|
| Acrylamide:N,N'-Methylenebisacrylamide | |
| 3-(Acryloyloxy)-2-hydroxypropyl methacrylate | $C_{10}H_{14}O_5$ |
| Bis[2-(methacryloyloxy)ethyl] phosphate | $C_{12}H_{19}O_8P$ |
| Bisphenol A propoxylate diacrylate | |
| 1,3-Butanediol diacrylate | $C_{10}H_{14}O_4$ |
| 1,4-Butanediol diacrylate | $C_{10}H_{14}O_4$ |
| 1,3-Butanediol dimethacrylate | $C_{12}H_{18}O_4$ |
| 1,4-Butanediol dimethacrylate | $C_{12}H_{18}O_4$ |
| N,N'-(1,2-Dihydroxyethylene)bisacrylamide | $C_8H_{12}N_2O_4$ |
| Di(trimethylolpropane) tetraacrylate average $M_w$ 466 | $C_{24}H_{34}O_9$ |
| Diurethane dimethacrylate | $C_{23}H_{38}N_2O_8$ |
| N,N'-Ethylenebis(acrylamide) | $C_8H_{12}N_2O_2$ |
| Glycerol 1,3-diglycerolate diacrylate | $C_{15}H_{24}O_9$ |
| Glycerol dimethacrylate | $C_{11}H_{16}O_5$ |
| Glycerol propoxylate (1PO/OH) triacrylate | |
| 1,6-Hexanediol diacrylate | $C_{12}H_{18}O_4$ |
| 1,6-Hexanediol dimethacrylate | $C_{14}H_{22}O_4$ |
| 1,6-Hexanediol ethoxylate diacrylate | |
| Hydroxypivalyl hydroxypivalate bis[6-(acryloyloxy)hexanoate] | $C_{28}H_{44}O_{10}$ |
| Neopentyl glycol diacrylate | $C_{11}H_{16}O_4$ |
| Neopentyl glycol propoxylate (1 PO/OH) diacrylate | $C_{11}H_{24}O_6$ |
| Pentaerythritol diacrylate monostearate | $C_{29}H_{50}O_7$ |
| Pentaerythritol tetraacrylate | $C_{17}H_{20}O_8$ |
| Pentaerythritol triacrylate | $C_{14}H_{18}O_7$ |
| Poly(propylene glycol) diacrylate | |
| Poly(propylene glycol) dimethacrylate | |
| 1,3,5-Triacryloylhexahydro-1,3,5-triazine | $C_{12}H_{15}N_3O_3$ |
| Tricyclo[5.2.1.0$^{2,6}$]decanedimethanol | $C_{18}H_{24}O_4$ |
| Trimethylolpropane ethoxylate (1 EO/OH) methyl ether | $C_{19}H_{32}O_8$ |
| Trimethylolpropane ethoxylate triacrylate average $M_n$ ~428 | |
| Trimethylolpropane ethoxylate triacrylate average $M_n$ ~692 | |
| Trimethylolpropane ethoxylate triacrylate average $M_n$ ~912 | |
| Trimethylolpropane propoxylate triacrylate average $M_n$ ~644 | $C_{33}H_{56}O_{12}$ |
| Trimethylolpropane triacrylate | $C_{15}H_{20}O_6$ |
| Trimethylolpropane trimethacrylate | $C_{18}H_{26}O_6$ |
| Tri(propylene glycol) diacrylate | $C_{15}H_{24}O_6$ |
| Tris[2-(acryloyloxy)ethyl] isocyanurate | $C_{18}H_{21}N_3O_9$ |

The polymer can be constructed into a variety of shapes and structures using techniques such as but not limited to extrusion, imprinting, spray coating, injection molding, braiding, weaving, knitting, molding, 3D printing, and machining.

In addition to using pH as a trigger for degradation, embodiments of this invention include responses to a variety of trigger mechanisms. For example, Chitosan dissolves in the presence of salt water and could be constructed to make an ear tube as well as many of the other embodiments mentioned in this document. Other potential triggers include, but are not limited to: Enzymes, Mechanical (i.e. ultrasound, vibration, force, etc.), Electrical, Temperature, Chemical reaction (i.e. alcohol, acid & base, solvent, etc.), and Physical (i.e. light, laser, magnetic field).

Figure 16:
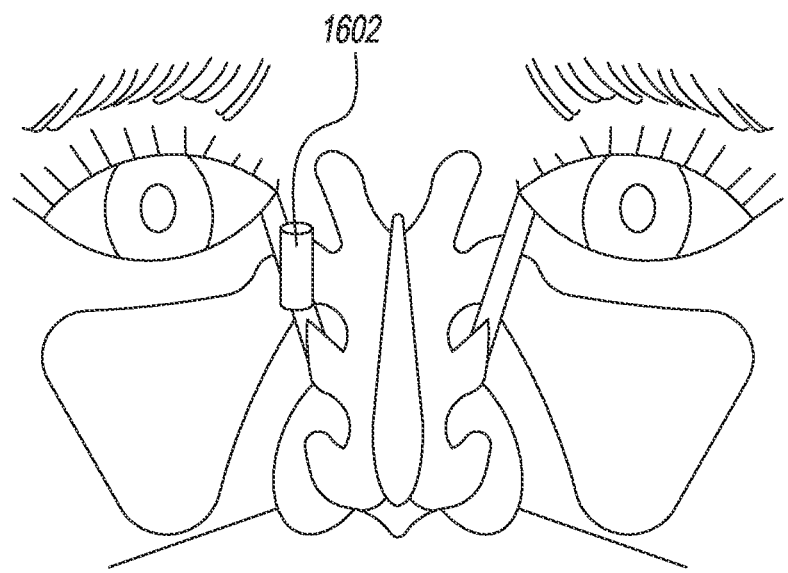
FIG. 16 illustrates an embodiment of application in sinus.

The use of the dissolvable on-command material is not limited to ear tubes. For example, in an exemplary embodiment, the material could be used in many ear, nose, and throat procedures where a temporary implant is needed. Such as a stent for treating sinusitis, as taught by U.S. Pat. No. 8,337,454 B2, (herein incorporated by reference in its entirety) in which a bio-absorbable, drug eluting, and shape memory polymer is used to construct a stent. With this on-command technology, as illustrated in FIG. 16, clinicians will have much better control of the life-span and functional period of an implant 1602 with a simple application a special nasal spray that will trigger the stent to dissolve.

In another exemplary embodiment, this technology could also be applied for esophageal and gastrointestinal implant and prosthesis, which are frequently used to treat malformation and strictures. There are frequent clinical situations in which esophageal and gastrointestinal stents should be removed, which often require surgical intervention. Nonsurgical stent removal has been difficult due to the embedding of the uncovered stent ends.

The on-command dissolvable materials can be used to manufacture these stents, and with an ingestion of a particular solution, inhalation of certain gas or mist, or introduction of a particular liquid through an enema procedure, the stent could be triggered to dissolve and obviate the need for other invasive removal methods.

Beyond stents, the present technology could be used to create implants for treating gastroesophageal reflux disease, gastro-intestinal by-pass devices for treating obesity and diabetes, and any device where it would be advantageous for the removal or disappearance of the foreign body after a period of time.

Figure 17:
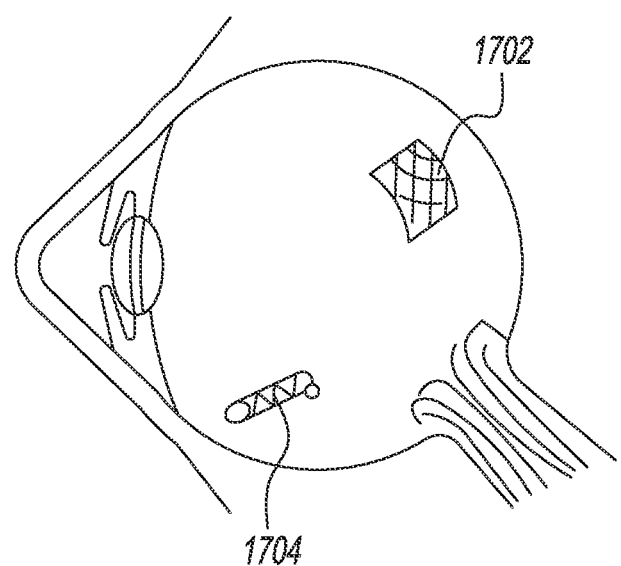
FIG. 17 illustrates an embodiment of application in opthamological uses.

In another exemplary embodiment, the present disclosure could be applied to ophthalmology. For instance, surgical solutions have been developed for treating glaucoma, which involves implanting a small shunt device. Referring to FIG. 17, on-command dissolvable materials could be adopted to create implants 1702 and 1704 that can be dissolved with an application of a specific eye drop that contains the triggering solution to dissolve the implants 1702 and 1704.

The present materials could be used to make sutures and stiches. When it is time to remove the sutures and stiches, a patch that contains the triggering solution could be applied to the wound, and trigger the suture/stiches to dissolve.

Figure 18:
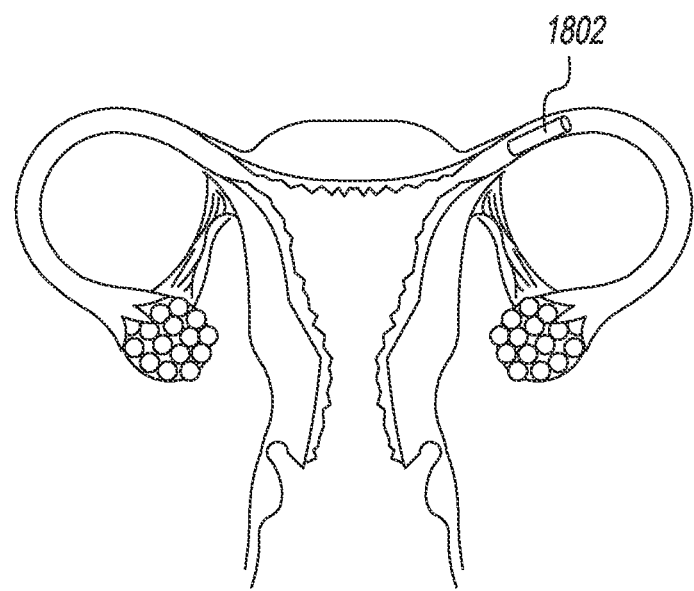
FIG. 18 illustrates an embodiment of application in gynecological uses.

The present disclosure could be applied to gynecological implants and prosthesis. The popularity of contraceptive implants has risen in recent years. However, some of these implants require removal when a woman wishes to conceive again. This can be an uncomfortable process and might require a visit to the doctor's office for removal. Providing a solution that the female could administer herself to dissolve the contraceptive provides significant advantages. Referring to FIG. 18, on-command dissolvable materials could be applied to include other gynecological implants 1802 in addition to contraceptive implants.

The present dissolvable on-command materials could also be used in urological applications. There are clinical needs for stents in the urinary tract as well as implants to restore continuity to the urinary tract. Permanent implants can lead to infection after tissue remolding has occurred. A dissolvable on-command option would allow the physician to monitor the tissue remolding and then noninvasively remove the implant through a catalyst, such as pH as mentioned above or another mechanism.

Figure 19:
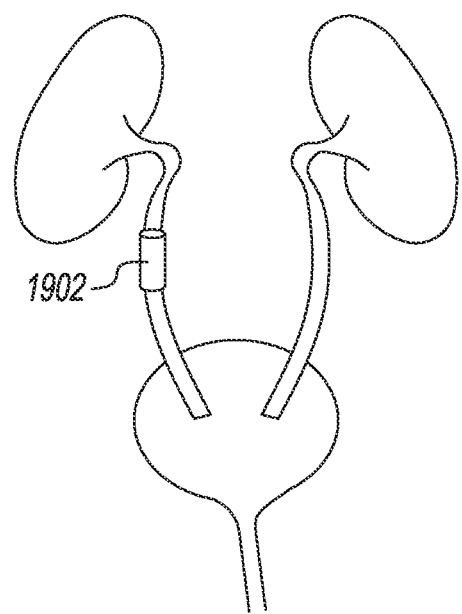
FIG. 19 illustrates an embodiment of application in urological uses.

There are also clinical indications for indwelling catheters, which require a follow up visit to remove. Referring to FIG. 19, a portion of the catheter 1902 or the entire catheter could be made from this dissolvable on-command material. This would avoid a follow up visit or at minimum reduce the pain and discomfort with catheter removal.

The present materials could also be used in oral implants to alleviate the need for sedation or pain management during the removal of oral prosthesis such as braces or other orthodontics.

These materials could also be used as dermal patches to either protect an area of interest or reduce discomfort when removing a device attached to the skin. Since the mechanical properties can be altered of this material, the material could be made to be quite hard and durable lending usefulness to applications such as a water proof cast that does not need a saw for removal.

Figure 20A:
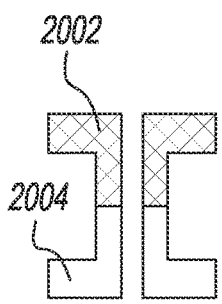
FIGS. 20A-20I illustrates a schematic of an ear tube with a nitrocellulose coating.
Figure 20D:
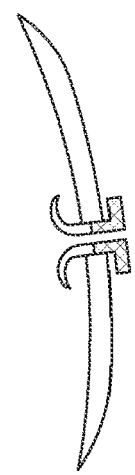
Figure 20B:
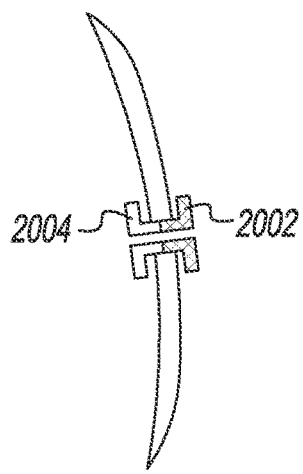
Figure 20E:
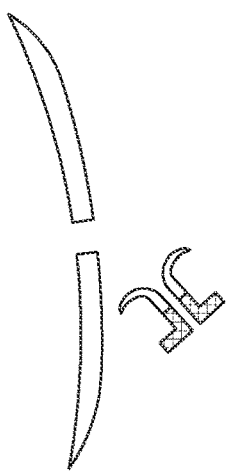
Figure 20C:
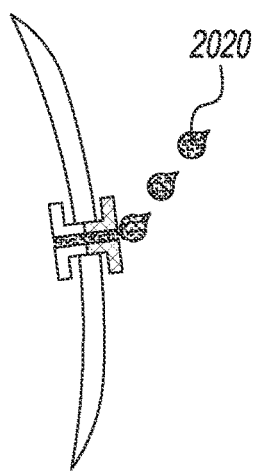
Figure 20F:
Figure 20G:
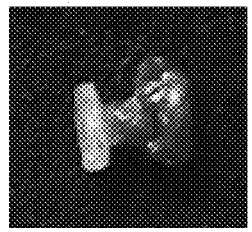
Figure 20H:
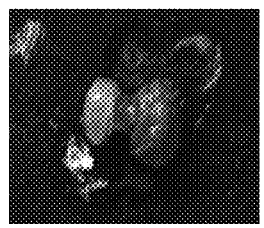
Figure 20I:
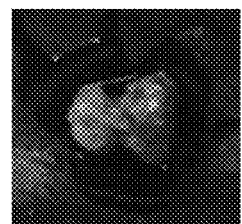
Figure 21A:
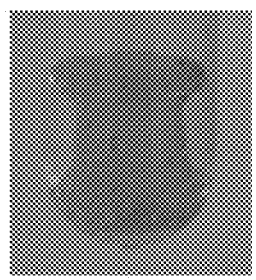
FIGS. 21A-21F illustrates an example of the ear tube prototypes dissolving in 70% ethanol.
Figure 21B:
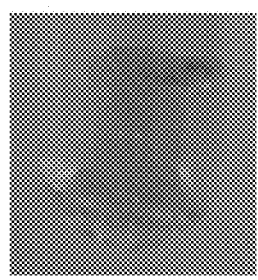
Figure 21C:
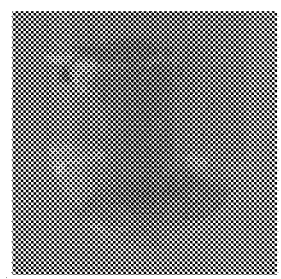
Figure 21D:
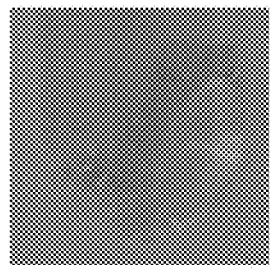
Figure 21E:
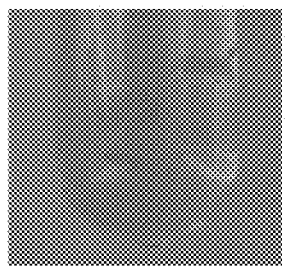
Figure 21F:
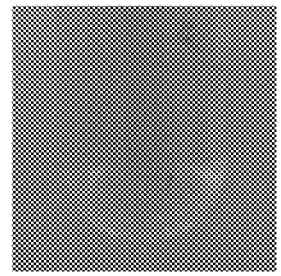

In an exemplary embodiment, an ear tube may have a nitrocellulose coating. As illustrated in FIG. 20A, one half of the tube 2000, or an outer portion 2002 of the tube 2000 is coated with a nitrocellulose coating. In FIG. 20B, the tube 2000 is implanted in the eardrum with the outer portion 2002 facing the ear canal and the inner portion 2004 facing the middle ear. In FIG. 20C, the triggering solution 2020 is administered to the tube 2000. FIG. 20D illustrated that the inner portion 2004 begins to soften, and in FIG. 20E, the tube 2000 is removed from the eardrum. FIG. 20F illustrates the eardrum beginning to heal after the removal of the tube 2000. Ideally, the bulk of the ear tube would fall in the ear canal where it can be easily cleared out. FIGS. 20G-20I illustrate a progressive dissolution of the tube 2000 after the tube has been placed in a mixture of ethanol and water. The portion without the nitrocellulose coating is readily dissolved and the part with the protective coating is left intact, as seen in FIGS. 20G-20I. The elapse time between each picture is 20 to 30 minutes. This embodiment provides significant advantages. For instance, as a result of the provided design as little material as possible falls into the middle ear due to dissolution (or softening) of the part of the ear tube situated in the middle ear. Because the bulk of the ear tube would fall in the ear canal where it can be easily cleared out, fewer issues arise with the tube.

According to another exemplary embodiment, the ear tube could be made out of a solid block of EUDRAGIT E-PO Polymer. The solid block of EUDRAGIT E-PO polymer is formed by melting EUDRAGIT E-PO polymer in its powder form in an aluminum mold at 150 degrees Celsius. The block is then cut into smaller elongated pieces. These pieces of solid polymer are machined by turning the polymer block on a micro turn machine to make flanges specific to the ear tube shape.

In another exemplary embodiment, the ear tube may be fabricated using EUDRAGIT E-PO polymer. The shape of the ear tube is printed in polymer using a 3D printer. From this positive duplicate of the ear tube, a negative mold in shape of the ear tube is fabricated using silicone. A small amount of EUDRAGIT E-PO polymer in its powder form is introduced in the negative mold and kept in the oven at 150 degrees Celsius for 10 minutes. This process is repeated until the mold is full of molten polymer. The mold is then cooled off and the ear tube extracted from the silicone.

In a further exemplary embodiment, a triggering solution of 70% ethanol is used. The 70% ethanol solution dissolves ear tube prototypes in approximately 30-90 minutes, depending on the size of the prototype. As illustrated in FIGS. 21A-F, the ear tube dissolves slowly over time in 20 minutes.

Figure 22A:
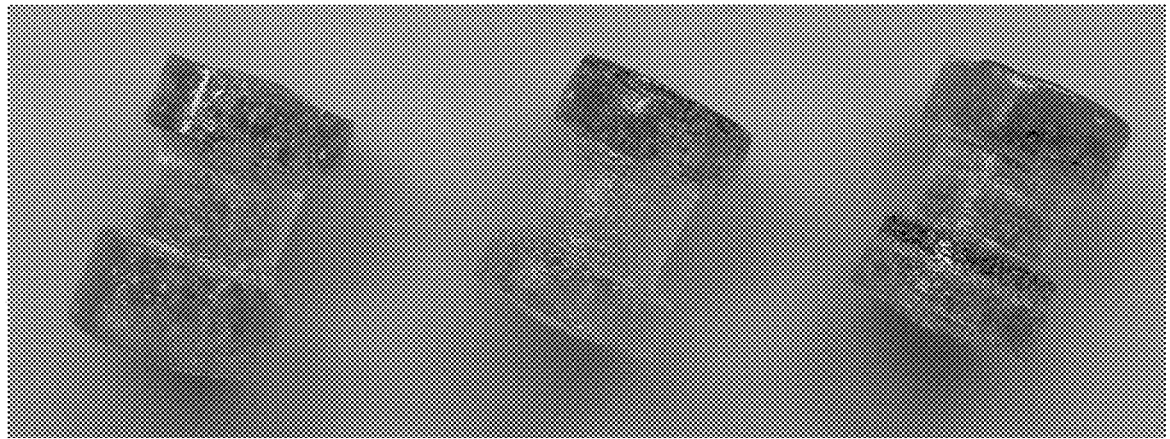
FIGS. 22A-22B illustrate ear tube prototypes that have been exposed to different environmental factors, FIG. 22A at 0 minutes and FIG. 22B at 70 minutes.
Figure 22B:
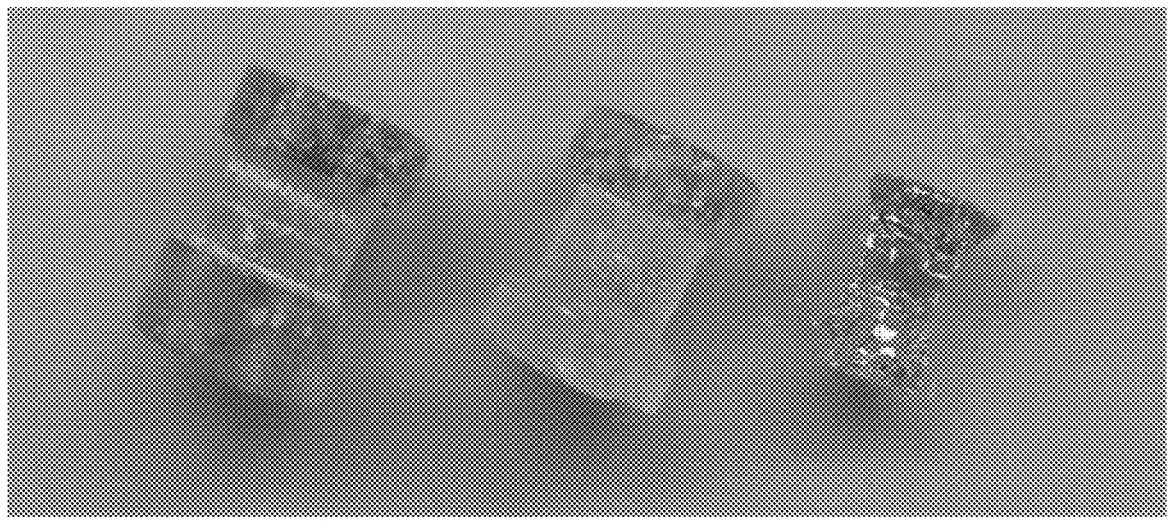
Figure 23:
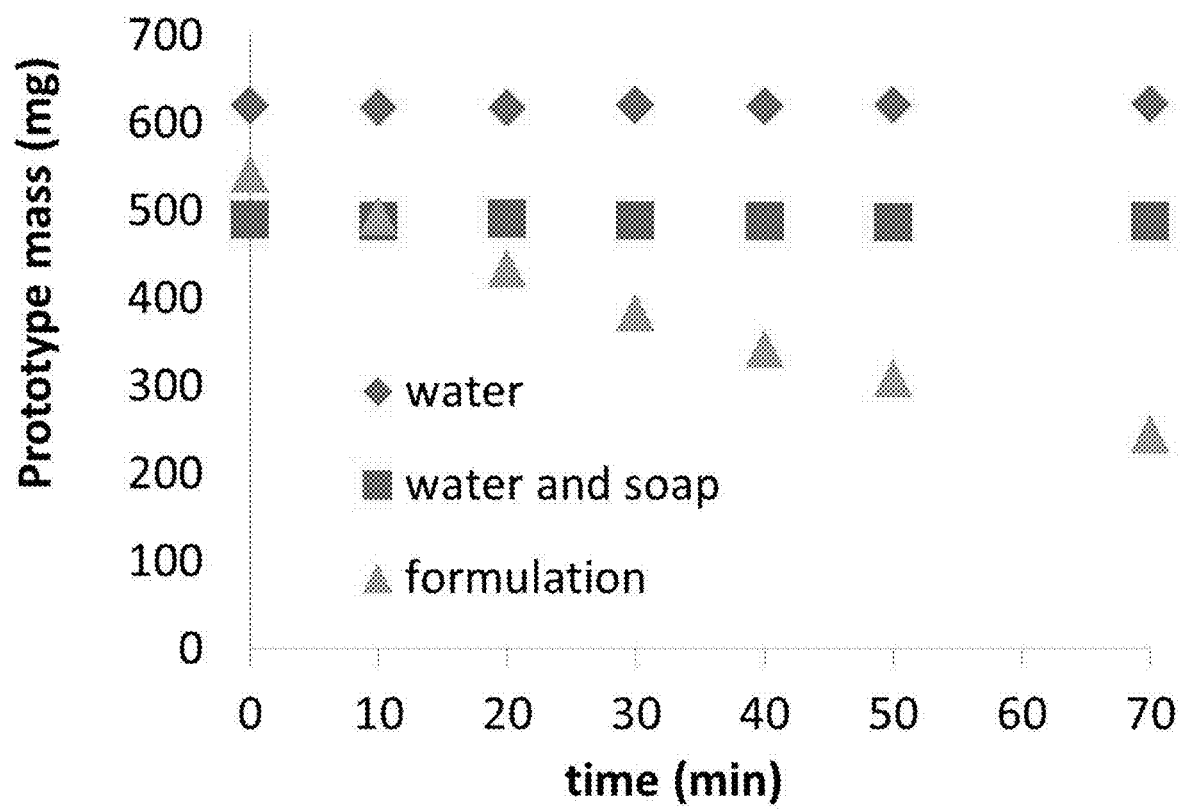
FIG. 23 illustrates a graph of the mass of ear tube prototypes when expose to different environmental factors.

The same prototypes are not affected by prolonged stay in water or waste mixed with soap (mimicking bath water or shower). FIG. 22A illustrates three different ear tubes before being exposed to different environmental factors. FIG. 22B illustrates the ear tubes after being exposed to these different factors for 70 minutes. The ear tube on the left in FIG. 22B was exposed to water, the ear tube in the middle was exposed to a mixture of soap and water, and the ear tube on the right was exposed to the 70% ethanol solution. These findings are summarized in a graph illustrated in FIG. 23. The ear tubes that were exposed to water, or soap and water maintained their mass over 70 minutes whereas the mass of the ear tube decreased when it was exposed to the 70% ethanol solution over 70 minutes.

Figure 24A:
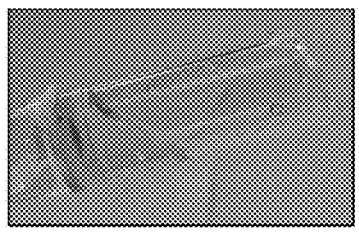
FIG. 24A-24F illustrate an example of a dissolution test in the artificial ear canal.
Figure 24B:
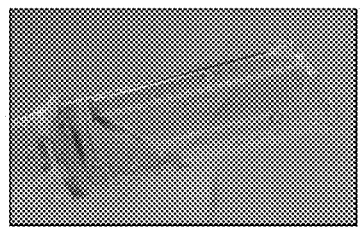
Figure 24C:
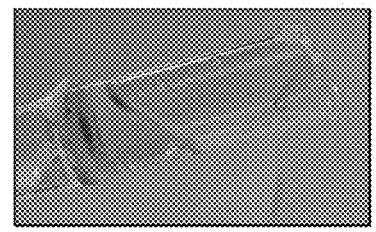
Figure 24D:
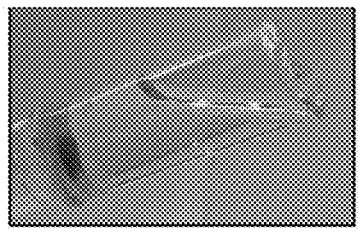
Figure 24E:
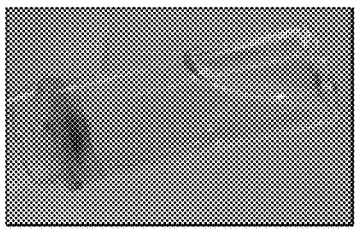
Figure 24F:
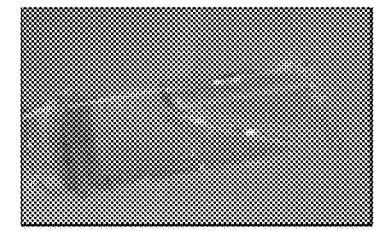
Figure 25:
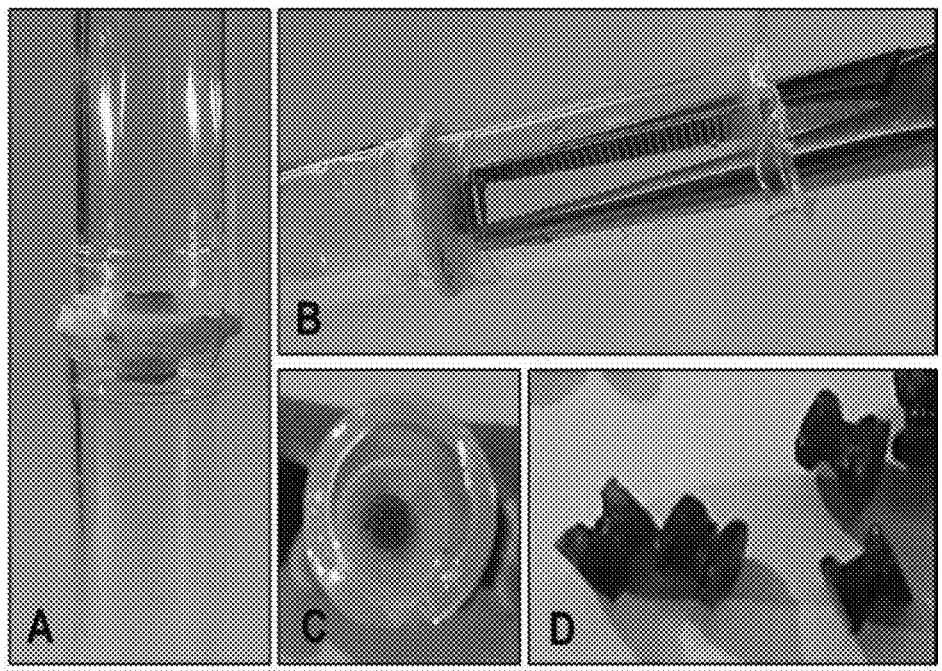
FIG. 25 illustrates an example of an ear tube placed in an artificial model of the ear canal and eardrum, (A) side view; (B) placement of the tube; (C) top view; (D) examples of prototypes.

A similar experiment was performed in a simulated eardrum/ear canal environment using water and an 80% Isopropyl alcohol solution. The results are illustrated in FIG. 24. FIGS. 24A-C illustrate the ear tube in water for 30 minutes. FIG. 24A is at 0 minutes, FIG. 24B at 15 minutes, and FIG. 24C at 30 minutes. FIGS. 24D-F illustrate the ear tube in 80% isopropyl alcohol for 30 minutes. FIG. 24D is at 0 minutes, 24E is at 15 minutes, and FIG. 24F is at 30 minutes.

According to an exemplary embodiment, the pH value needed to trigger the degradation in the proposed polymer is between 1.5 and 5, which will not pose any health concern. The pH values of 15 commonly used topical ear drop formulations listed below in Table 10 ranged from 2.89 to 7.83. A conventional ear drop formulation with low enough pH value or a combination of several could be used to trigger the on-command dissolve process. Other chemicals could be combined together to speed the process, such as saline, alcohol, isopropry alcohol or acetone that would provide dispersive, ionic, polar, or H-Bond interactions. Other local anesthetics, such as liquid lidocaine could also be added to the solution to improve the comfort of the procedure.

TABLE 10 pH value of commonly used ear drops formulations

| Product | pH Value |
|---|---|
| Acetic acid 2% | 2.89 |
| Dexamethasone 0.1%, neomycin sulfate 3,250 units/ml, acetic acid 2% | 3.00 |
| Hydrogen peroxide 6% | 3.00 |
| Aluminum acetate 13% | 3.18 |
| Aluminum acetate 8% | 3.40 |
| Triamcinolone acetonide 0.1%, neomycin undecenoate 0.35% | 4.38 |
| Glycerin and ichthammol 10% | 4.90 |
| Ciprodex Otic | 5.00 |
| Hydrocortisone 1%, neomycin sulfate polymyxin B sulfate 10,000 units/ml | 5.50 |
| Framycetin sulfate 0.5%, gramicidin 0.005%, dexamethasone 0.05% | 5.53 |
| Gentamicin sulfate 0.3%, hydrocortisone acetate 1% | 6.18 |
| Floxin Otic | 6.50 |
| Flumetasone pivalate 0.02%, clioquinol 1% | 7.14 |
| Betamethasone sodium phosphate 0.1%, neomycin sulfate 0.5% | 7.28 |
| Prednisolone sodium phosphate 0.5% | 7.74 |
| Betamethasone sodium phosphate 0.1% | 7.70 |
| Prednisolone sodium phosphate 0.5%, neomycin sulfate 0.5% | 7.83 |

Source: Eng, Chee-Yean, and Amged S. El-Hawrani. "The pH of commonly used topical ear drops formulations in the treatment of otitis externa." Ear Nose and Throat Journal 90.4 (2011): 160, hereby incorporated by reference in its entirety.

At the desired time, ear drop formulations with an acidic solution such as citric or acetic acid (pH=2-3) are introduced to the ear tube. The acidic aqueous solution reacts with the amine groups. At pH<5, the tertiary amine on the 2-(Dimethylamino)ethyl methacrylate group is protonated and makes increase the hydrophilicity of the polymeric chain. By incorporating more water molecules in between the chains, the co-polymer swells, losing its mechanical properties and to eventually dissolves the ear tube. The co-polymer of the ear tube can be engineered to possess the desired mechanical properties, including rigidity, stability and solubility in the acidic solution. For example, the fabrication process may vary the amount of each monomer during the synthesis of the polymer. The co-polymer makeup of the ear tube design can be engineered to dissolve over the desired period of time, anywhere from a few minutes to few days.

Figure 13A:
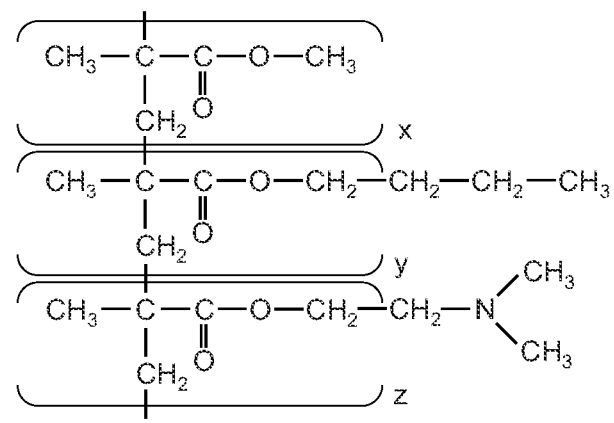
FIG. 13A illustrates a chemical structure of methacrylate-based co-polymer.
Figure 13B:
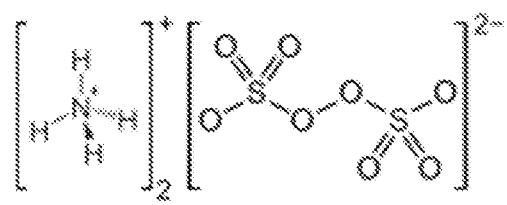
FIG. 13B illustrates a chemical structure of ammonium persulfate.
Figure 15:
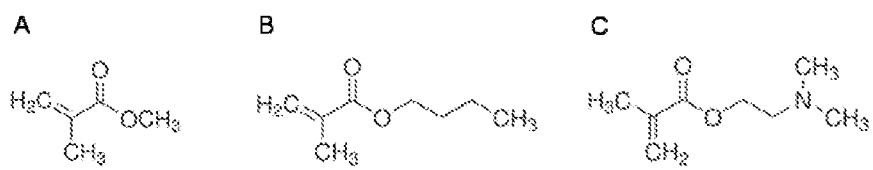
FIGS. 15A-15C illustrates commercially available monomers for co-polymer synthesis.
Figure 14:
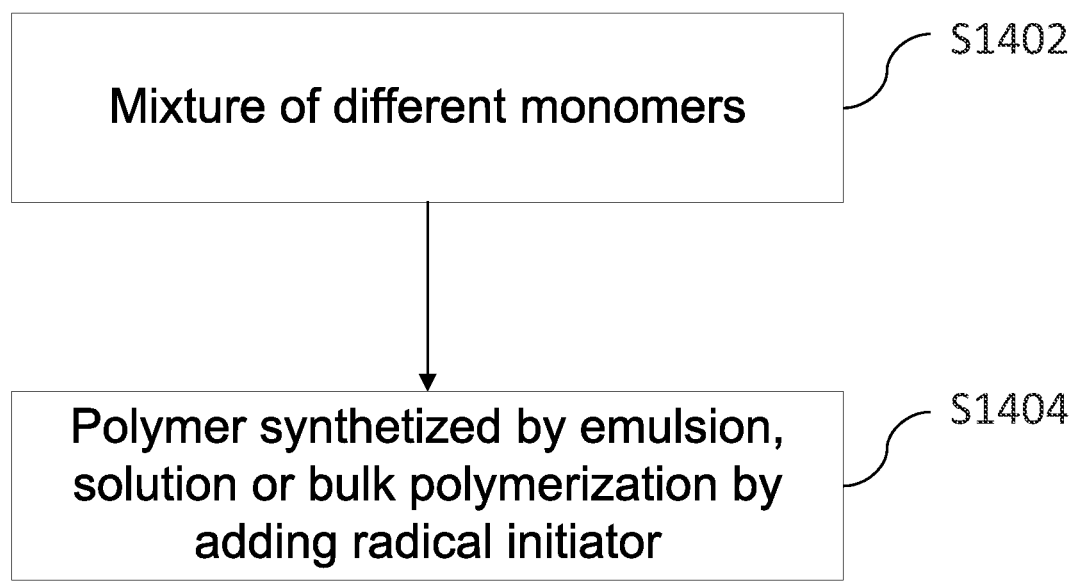
FIG. 14 illustrates a flowchart of the fabrication of the co-polymer.

In an exemplary embodiment, the ear tube may be fabricated from a mixture of different monomers. For example, the material composing the ear tube is a statistical co-polymer that includes of 3 different monomers, as illustrated in FIG. 13A. The relative percent of each polymer may range from 0 to 100%, with a total of 100%. FIG. 14 illustrates a flowchart of the fabrication process. In S1401, the monomers are mixed together. The mechanical properties are tuned by the percentage of methyl methacrylate and butyl methacrylate moieties and dissolution properties by the percentage of (Dimethylamino)ethyl methacrylate. In step 1402, the co-polymer is synthesized either by emulsion, solution or bulk polymerization by adding a radical initiator such as ammonium persulfate, the chemical structure illustrated in FIG. 13B, to a mixture of methyl methacrylate, butyl methacrylate, and 2-(Dimethylamino)ethyl methacrylate. For example, a mixture of 25% methyl methacrylate, 25% butyl methacrylate and 50% 2-(Dimethhylamino)ethyl methacrylate could be used. The chemical structure for methyl methacrylate is illustrated in FIG. 15A, the chemical structure for butyl methacrylate is illustrated in FIG. 15B, and the chemical structure for 2-(Dimethylamino)ethyl methacrylate is illustrated in FIG. 15C.

In particular, the E-PO polymer is manufactured through a bulk polymerization process to produce polymer granules and further milled into powder form. The E-PO polymer exhibits good solvability in acetone. As the solvent evaporates, the liquid mixture becomes a sticky pliable material which can be easily shaped and molded into the desired structure. When the solution in the mixture completely evaporates, the residue polymer becomes a solid and hard material, showing good mechanical and structural strength. Through this dissolve-and-dry process, the E-PO polymer transforms from powder form into solid bulk and still maintains its original chemical properties. For example, it can be dissolved by ethanol again, though at a much slower rate, given that it now has much less surface area compare to powder form.

The chemical profile and physical property of the EUDRAGIT® E-PO polymer presents itself as a good candidate for the intended applications for the following reasons: (1) the polymer class is FDA approved for medical applications and considered non-toxic; (2) it is only water soluble in low pH environment (pH 1.0-4.0), which means it is non-dissolvable or stable in most human implants environments, which is usually pH neutral; (3) it can be easily dissolved in ethanol or isopropyl alcohol (IPA), which is considered non-toxic/minimal risk for medical applications; (4) it can be easily shaped and milled into the desired structure with low-cost/low-tech equipment; and (5) it has good mechanical strength as a medical implant material As discussed, when the E-PO polymer is dissolved in acetone the result is in liquid form. Once in the correct shape, the acetone needs to be evaporated out of the construct yielding a solid form. Since the acetone solution is viscous, air bubbles are prone and can make the final product brittle. To remove the air from the mixture, it should be exposed to a vacuum prior to setting into a particular shape. Using the ear tube application as a specific example, the polymer can be made into the standard ear tube shape through the dissolve-and-dry process. It can be molded into the desired shape when the polymer is still soft and pliable, or milled when it's completely dry and hardens. Other polymers or materials can be added to adjust the desired mechanical property, such as but not limited to, degradation rate, hardness and elasticity. Other pharmaceutical ingredients or drugs could also be added for therapeutic purposes.

Obviously, numerous modifications and variations of the present invention are possible in light of the above teachings. It is therefore to be understood that within the scope of the appended claims, the invention may be practiced otherwise than as specifically described herein.

What is claimed is:

1. A dissolvable on-command tympanostomy tube that is insertable into an eardrum of an ear of a patient, comprising:
a tube having two flared ends, wherein
the tube is comprised of a first material that is configured to be insoluble in bodily fluids of the patient but disintegrate upon intentional contact with a second material introduced from an extracorporeal environment into the ear of the patient, the disintegration being based on a chemical reaction between the first material and the second material,
the two flared ends include an inner flange and an outer flange, the inner flange and the outer flange being connected by a connecting member having a through-hole that extends from the inner flange through the connecting member to the outer flange, and
the inner flange is made of a third material that is biodegradable.

2. The dissolvable on-command tympanostomy tube of claim 1, wherein the inner flange has a larger diameter than the outer flange.

3. The dissolvable on-command tympanostomy tube of claim 1, wherein the inner flange is tailed.

4. The dissolvable on-command tympanostomy tube of claim 1, wherein
an inner portion including the inner flange and a portion of the connecting member adjacent to the inner flange are made of the first material, and
an outer portion including the outer flange and a remaining portion of the connecting member are made of a third material, the third material being biodegradable.

5. The dissolvable on-command tympanostomy tube of claim 1, wherein
at least one of the inner flange and the outer flange are made of the first material and the connecting member is made of a fourth material, the fourth material being configured to disintegrate when in contact with the second material according to a chemical reaction between the fourth material and the second material, and
the first material degrades faster than the fourth material when both the first material and the fourth material are in contact with the second material.

6. The dissolvable on-command tympanostomy tube of claim 1, wherein a portion of the connecting member that is adjacent to the outer flange has a greater thickness than a thickness of a portion of the connecting member that is adjacent to the inner flange.

7. The dissolvable on-command tympanostomy tube of claim 1, wherein an inner portion including the inner flange and a portion of the connecting member adjacent to the inner flange contains a plurality of micro-cavities.

8. The dissolvable on-command tympanostomy tube of claim 1, wherein a portion of the connecting member adjacent to the inner flange contains a plurality of micro-cavities.

9. The dissolvable on-command tympanostomy tube of claim 1, wherein the inner flange has a coating made of the first material.

10. The dissolvable on-command tympanostomy tube of claim 1, wherein an outer portion including the outer flange and a portion of the connecting member adjacent to the outer flange is coated with a nitrocellulose coating.

11. The dissolvable on-command tympanostomy tube of claim 1, wherein the first material is a mixture of methyl methacrylate, butyl methacrylate and 2-(Dimethylamino) ethyl methacrylate.

12. The dissolvable on-command tympanostomy tube of claim 1, wherein the second material is a liquid with a pH between 2.89 and 5.

13. The dissolvable on-command tympanostomy tube of claim 1, wherein an inner portion of the tube degrades more rapidly than an outer portion of the tube upon the contact with the second material.

14. The dissolvable on-command tympanostomy tube of claim 1, wherein the second material is ethanol.

* * * * *